United States Patent [19]
Rinderle et al.

[11] Patent Number: 6,084,072
[45] Date of Patent: Jul. 4, 2000

[54] PURIFIED LECTIN AND METHODS OF USE

[75] Inventors: Stephen J. Rinderle, Hilliard, Ohio; Irwin J. Goldstein, Ann Arbor, Mich.

[73] Assignee: The Regents of the University of Michigan, Ann Arbor, Mich.

[21] Appl. No.: 08/041,287

[22] Filed: Mar. 30, 1993

Related U.S. Application Data

[63] Continuation of application No. 07/605,040, Oct. 29, 1990, abandoned, which is a continuation-in-part of application No. 07/586,560, Sep. 21, 1990, abandoned, which is a continuation-in-part of application No. 07/508,202, Apr. 11, 1990, abandoned.

[51] Int. Cl.$^7$ .................................................. C07K 14/42
[52] U.S. Cl. ......................... 530/370; 436/827; 530/372; 530/396
[58] Field of Search ............................. 436/827; 530/320, 530/372, 396

[56] References Cited

U.S. PATENT DOCUMENTS 4,742,046   5/1988   Bliah ............................................ 514/8

FOREIGN PATENT DOCUMENTS 63038   3/1989   Japan ...................................... 530/396

OTHER PUBLICATIONS

Arora et al, "Occurrence and Characterzation of Lympho–Agglutinins in Indian Plants." *Vox. Sang.* 52:134–137 (1987).

Program of the Ann. Meeting of the Am. Gastroenterological Assoc. and Digestive Disease Week, May 13–19, 1989, Washington, D.C. p. A417.

Neurath et al, eds., *The Proteins*, 3$^{rd}$ ed., vol. I. Academic Press. 1975, pp. 162–165.

Rinderle et al, "Isolation and Characterization of Amaranthin, a Lectin Present . . . ". *J. Biol. Chem.* 264(27) Sep. 25, 1989. pp. 16123–16131.

Koeppe et al. Purification and Characterization of a Lectin . . . J. Food Sci. vol. 53, No. 5, pp. 1412–1417. 1988.

Sandhu et al. Occurrence and Characterization of Phytolectins . . . Lectins—Biology, Biochemistry, Clinical Biochemistry, vol. II, pp. 679–692, 1982.

Sandhu et al. Further Studies on Sperm–Reactive Lectins . . . Lectins. vol. IV, pp. 547–557, 1985.

J. Chromatography, vol. 215, issued 1981, Les et al, "Affinity Chromatography for the Purification of Lectins", pp. 361–372.

*Primary Examiner*—Jeffrey E. Russel
*Attorney, Agent, or Firm*—Harness, Dickey & Pierce, P.L.C.

[57] ABSTRACT

Amaranthin, a new lectin isolated from the seeds of *Amaranthus caudatus*, is purified and characterized. Amaranthin, designated ACA (*Amaranthus caudatus* agglutinin), has a high affinity for the T-antigen glycoconjugate and variants thereof expressed by proliferating colorectal epithelium. ACA selectively binds glycoconjugates in the lower half of the colonic crypt and is useful as a marker of colonic epithelial cell differentiation in the human colon. ACA also binds to glycoconjugates in neoplastic colonic tissues, and binds to preneoplastic polypoid and flat colonic tissue from patients with familial polyposis coli. ACA is also readily adapted for quantitative measurement of lectin-binding sites. ACA binding assays can thus be used for detecting early stage abnormalities of proliferation and differentiation in normal-appearing preneoplastic colorectal epithelium and to diagnose neoplastic premalignant and malignant colorectal lesions.

2 Claims, 3 Drawing Sheets

Gal β1,3 GalNAcα 1 ⟶ O Ser/thr

Gal β1,3 GalNAcα 1 ⟶ O Ser/thr

PURIFIED LECTIN AND METHODS OF USE

RELATED APPLICATIONS

This is a continuation of U.S. application Ser. No. 07/605,040 filed Oct. 29, 1990, which is a continuation-in-part of U.S. application Ser. No. 07/586,560 filed Sep. 21, 1990, which is a continuation-in-part of U.S. application Ser. No. 07/508,202 filed Apr. 11, 1990, now abandoned.

This invention was made with government support under Grant No. GM 29470 awarded by the National Institute of General Medical Sciences and Grant No. CA 39233 awarded by the National Cancer Institute. The government has certain rights in the invention.

FIELD OF THE INVENTION

The present invention relates generally to a lectin isolated from *Amaranthus caudatus* and, more specifically, to the purified lectin, its method of extraction and purification and its use in detecting abnormalities of proliferation and differentiation of the colorectal epithelium.

BACKGROUND OF THE INVENTION

There are numerous means for identifying malignant colorectal lesions. However, no satisfactory probes are presently available to assess the malignant risk of premalignant neoplastic lesions, and methods currently used to detect abnormal proliferation in normal-appearing, preneoplastic epithelium require freshly obtained tissue, incubation in organ culture and autoradiography with a 2–4 week development period.

The use of lectin-based diagnostic testing circumvents the requirement for fresh tissue specimens. For example, the lectin PNA (peanut agglutinin) binds to and can be used to identify premalignant lesions in previously obtained formalin-fixed biopsy specimens. A series of synthetically-modified oligosaccharides was used to determine the specific sites of interaction between PNA and the T-antigen as reported in Rinderle, Stephen J., et al., (1989) *J.Biol. Chem.*, 264:16123–131. Experiments have demonstrated that PNA would bind T-antigen even if the C-6 hydroxyl group of N-acetylgalactosamine (GalNAc) was substituted.

The PNA lectin has been an important probe used by histochemists interested in colorectal neoplasia. See Koeppe, S. J., and Rupnow, J. H. (1988) *J. Food Sci.* 53, 1412–1417 and Springer, G. F., Desai, P. R., and Banatwala, I. (1975) *J. Natl. Cancer* Inst. 54, 335–339. PNA does not bind readily to mucins found in the normal colon, but binds to mucin secreted by colon cancers, reported in Koeppe and Kaifu, R., Plantefaber, L. C., and Goldstein, I. J. (1985) *Carbohydr. Res.* 140, 37–49. In addition, PNA binds to glycoconjugates present in a variety of premalignant lesions in the colon. Cooper has reported that the treatment of histological sections of human colonic tissue with neuraminidase resulted in the "unmasking" of cryptic T-antigens to which PNA is subsequently bound. However, this has not been the experience of all investigators, see Koeppe above.

Moreover, a series of oligosaccharides isolated from the mucin of normal human colonic tissues revealed no evidence of the T-antigen or its sialylated variants according to Shibata, S., Peters, B., Roberts, D. D., Goldstein, I. J., and Liotta, L. A. (1982) *FEBS Lett.* 142, 194–198 and Distler, J. J., and Jourdian, G. W. (1973) *Biol. Chem.* 248, 6772–6780.

Thus, it is not clear whether a variant form of T-antigen may be synthesized in normal colonic tissues. PNA, however, binds these lesions at a relatively late stage of neoplastic development, and is thus not useful in detecting early stage preneoplastic abnormalities. The usefulness of other lectins such as BPA (*Bauhinea purpurea* agglutinin) and RCA, (*Ricinis communis* agglutinin) is also limited in that their binding specificities are relatively broad and impede accurate interpretation of binding results.

The Thomsen-Friedenreich antigen (T-antigen) has been proposed as a specific carcinoma marker. See Springer, *J. National Cancer Inst.* and Springer, G. F. (1984) *Science* 224, 1198–1206. Thus, the development of well-defined, T-specific probes would lead to increased understanding and detection of certain types of cancer. Lectins once identified and isolated, remain particularly attractive as histochemical probes because reliable and uniform preparations of agglutinin can be easily generated and binding specificity can be documented with a high degree of precision. Thus, lectins which can detect early stage proliferation abnormalities in colorectal epithelium would be advantageous in screening normal-appearing preneoplastic epithelium to identify those at risk for colorectal cancer, and for diagnosing premalignant and malignant neoplastic lesions.

SUMMARY OF THE INVENTION

Amaranthin, a new and useful lectin is now isolatable to a high degree of purity from the seeds of the South American plant *Amaranthus caudatus*. Amaranthin has a high binding affinity for the T (Thomsen-Friedenreich) antigen glycoconjugate and sialylated variants associated with colorectal epithelial proliferation. Amaranthin, designated hereinafter as ACA (*Amaranthus caudatus* agglutinin), has a subunit molecular weight of from approximately 33,000 to about 36,000 daltons and probably exists as a homodimer since its native mass is measured to be about 63,500 daltons. It has one binding site per monomer, which confers its agglutination properties.

ACA is extracted from the seeds of the *Amaranthus caudatus* plant by fractionation, extraction, precipitation, and separation using a diethylaminoethyl (DEAE) cellulose followed by affinity chromatography on Synsorb-T beads, a trademarked product commercially available from Chembiomed Ltd., Alberta, Canada. Amaranthin has been characterized by a number of methods sufficient for its identification.

The availability of a new probe for the T-antigen which is capable of recognizing variations in the T-antigen which were not previously shown to be recognized by PNA is of great value as a histochemical probe of human colonic tissues. Specimens of normal human colon, neoplastic human colon, and a series of potentially premalignant lesions were examined using this lectin to determine whether a variant form of T-antigen was responsible for some of the above described controversies. ACA binds selectively in the portion of the colonic crypt where epithelial cell proliferation ordinarily occurs, binds to a variety of neoplastic lesions, and recognizes glycoconjugates in certain potentially premalignant tissues.

ACA binds selectively in the lower half of the colonic crypt of Lieberkühn, the proliferative zone of normal colonic epithelia, and is thus useful as a marker of colonic epithelial cell differentiation. ACA also binds to glycoconjugates in neoplastic colorectal lesions, including small adenomas, and to certain preneoplastic premalignant tissues, including polypoid and flat colonic tissue from FAP and HNPCC patients who are at risk for colorectal cancer. ACA also recognizes variants of the T-antigen that are not recognized by the closely related T-antigen-binding lectin PNA. For example, ACA recognizes T-antigen with substituents on the C1–3 position of galactose of the C-6 position of GalNAc.

In accordance with the principles of the present invention, ACA is extracted from the seeds of *Amaranthus caudatus*. The binding of the extracted ACA to glycoconjugates expressed by proliferating colorectal epithelium is used to detect zones of inappropriate cell proliferation. ACA binding is thus useful in screening normal-appearing preneoplastic epithelium to identify those at risk for developing neoplastic and malignant conditions at an early stage, and in diagnosing neoplastic premalignant and malignant colorectal lesions. Additionally, ACA binding is useful in monitoring the impact of preventive programs and treatment on colorectal epithelial cell proliferation. Enzyme-linked assays and assay kits for detecting ACA-glycoconjugate binding are also provided to facilitate screening and diagnosis in accordance with the principles of the present invention.

DETAILED DESCRIPTION OF THE PREFERRED EMBODIMENTS

Figure 1:
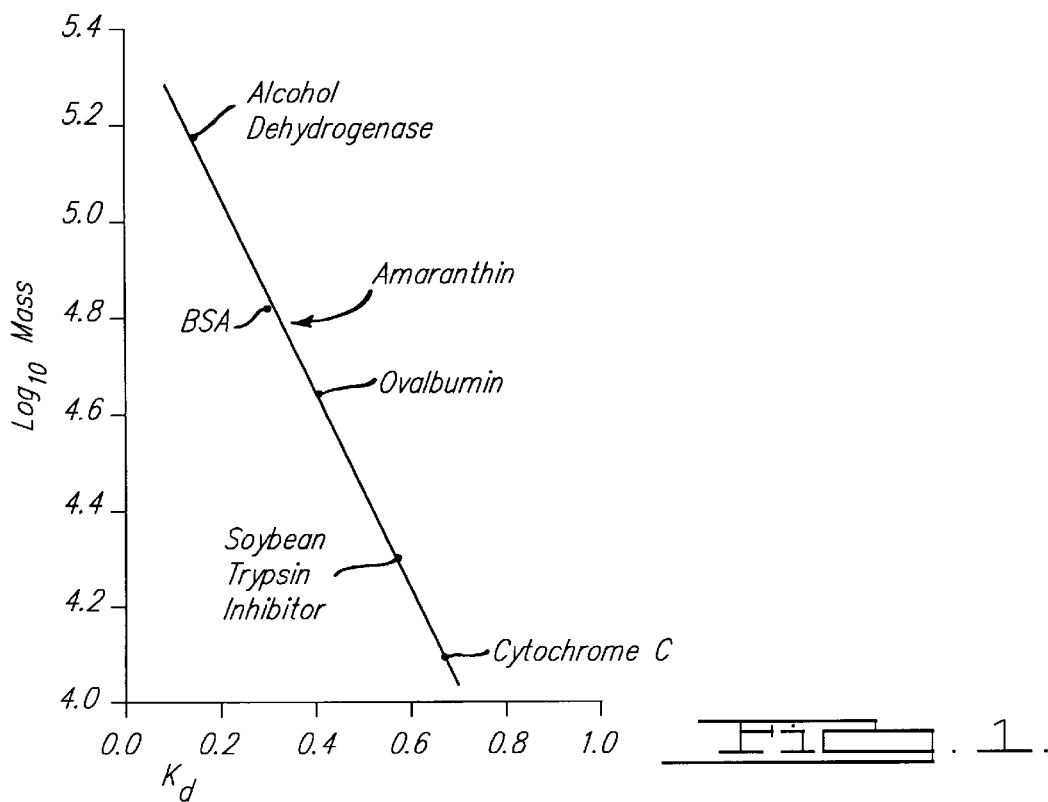
FIG. 1 is a graph illustrating molecular weight determination of ACA.

*Amaranthus caudatus* is an ancient plant native to the Andean countries of South America where it was once used as an important food source. See National Research Council (1984) *Amaranth: Modern Prospects for an Ancient Crop*. National Academy Press, Washington, D.C. There are over 60 known species of the genus Amaranthus. Although today the amaranth plant is used principally for ornamental purposes in the United States and Europe, a renewed interest in several Amaranthus species has been expressed due to their nutritional value as reported above, and in Vietmeyer, N. D. (1986) *Science* 232, 1379–1384. In 1970, Pardoe and co-workers reported that aqueous extracts of A caudatus seeds contained a lectin which agglutinated A, B, and O red blood cells equally well. See Pardoe, G. I., Bird, W. G. Uhlenbruck, G., Sprenger, I., and Heggen, M. (1970) *Immunotaestforsch. Allerg. Klin. Immunol.* 140, 374–394. However, these investigators did not isolate the lectin or define the sugar-binding specificity of the lectin.

Recently, the isolation of lectins from two Amaranthus species has been described. Zenteno, E., and Ochoa, J. L. (1988). See *Phytochemistry* 27, 313–317, purified a lectin from *A.leucocarpus* by chromatography on a blood group A stroma column. These investigators reported the lectin to have subunit mass equivalent to 45,000 daltons, and to be inhibited best by N-acetylgalactosamine and fetuin. The *A. leucocarpus* lectin was also found to be mitogenic to mouse spleen lymphocytes. In contrast, Pardoe et al. reported that a crude extract of *A. caudatus* seeds was non-mitogenic to hog lymphocytes.

Koeppe and Rupnow described the purification of a lectin from the seeds of *A. cruentus* using affinity chromatography on fetuin-agarose. The *A. cruentus* lectin had a subunit mass of 35,000 daltons and a native mass of 66,000 daltons suggesting that this lectin occurs as a homodimer. It was also found to be best inhibited by N-acetylgalactosamine and fetuin. Polyclonal antibodies against the purified *A. cruentus* lectin gave a reaction of identity with crude seed extracts from various Amaranthus species, including *A. caudatus*. The T-antigen (GalB1,3GalNAca-O-radical) has been proposed as a specific carcinoma marker as stated above. The isolation, purification and characterization of the T-(or cryptic T) antigen-specific lectin from the seeds of *Amarenthus caudatus* is utilizable to identify problem tissues much earlier than markers currently available. The purification scheme set out herein is applicable to any Amaranthus genus.

STARTING MATERIALS

*Amaranthus caudatus* seeds were purchased from DeGiorgi Brothers Company, Council Bluffs, Iowa. Most sugars were purchased from Pfanstiehl Laboratories of Waukegan, Ill. or Sigma Corporation. Diethylaminoethyl (DEAE)-cellulose (0.87 meq/g) was purchased from Sigma Corp of St. Louis, Mo. Sephadex G-200 (superfine) was obtained from Pharmacia of Uppsala, Sweden. Fresh human red blood cells (A, B, and O) were obtained from Dr. W. J. Judd, University of Michigan; Galβ1,3GalNAcα-O—(CH$_2$)$_8$ CONH-Synsorb (Synsorb-T), GalNAcα1, 3GalNAcβ1-O—(CH$_2$)$_8$COOCH$_3$, Galβ1, 3GalNAcα-O—(CH$_2$)$_8$ OOH$_3$, Galβ1 3GalNAcα-, and β-bovine serum albumin (BSA) glycoconjugates, NeuAcα2,3Galβ1, 3GalNAcα-O-BSA, Galβ1,3[NeuAcα2,6]GalNAcα-O-BSA, NeuAcα2,3Galβ1,3GalNAcα-O—(CH$_2$)$_8$COOCH$_3$, type A trisaccharide-, bovine serum albumin and Galβ1,3 (2-acetamido-2-deoxy-1,5-anhydro-D-galactitol) were generous gifts of Dr. R. M. Ratcliffs of Chembiomed Ltd., of Alberta, Canada.

Galβ1,3GalNAcα-O—O-nitrophenyl,Galβ1,3GalNAcα-O—CH$_2$CH=CH$_2$, Galβ1,3GalNAcβ-o-CH$_2$CH=CH$_2$, Galβ1,3GalNAcβ1,Galβ-O—CH$_3$ GlcNAcβ1,3Galβ1, 3GalNAcα-O-benzyl, Galβ1,3[6-F]GalNAcα-O-benzyl, GlcNAcβ1,3[6-F]GalNAcα-O-benzyl, Galβ1,3GalNAcα-O-benzyl, D-Fucβ1,3GalNAcα-O-Benzyl, and 3-O-methyl Galβ1,3GalNAcα-O-benzyl were made available by Dr. K. L. Matta of Roswell Park Memorial Institute, New York State Department of Health.

The following carbohydrates were prepared by Dr. R. Kaifu: methyl(2-N-p-nitrobenzamido)α-GalN, methyl(2-N-benzamido)α-Gal;N, methyl(2-O-nitrobenzoate)α-Gal, methyl(2-O-acetyl)α-Gal, and methyl(2-deoxy)αGal as described in Kaifu, R., Plantefaber, L. C., and Goldstein, I. J. (1985) *Carbohydr. Res.* 140. 37–49, 3-O-(2-N-Acetyl-α-D-galactopyranosyl)-N-(benzylox-carbonyl)-L-serine methyl ester was prepared as described in Ferrai, Galβ1, 3Galα-O—CH3 as per Kovac, P., Glaudemans, C. P. J. and Taylor, R. B. (1985) *Carbohydr. Res.* 142, 158–164, and the disaccharides GalNAcα1,3Gal and GalNAα1, 6Gal as per Lemieux, R. V., Ito, Y., James,. K., and Nagalbhushan, T. L. (1973) *Can. J. Chem.* 51, 7–18 and Lemieux, R. V., and Stick, R. V. (1978) *Aust J. Chem* 31, 901–905 and were prepared by N. Plessas.

Galβ1,3GalN Acα-O-CH$_3$ and Glcβ1,3GalNAcα-O—CH$_3$ (starting with Glc and GalNAcα-O—CH$_3$) were synthesized according to Flowers and Shapiro. See Flowers, H. M., and Shapiro, D. (1965) *J. Org. Chem.* 30, 2041–2043. All sugars are in the pyranose configurations. PNA was donated by Dr. A. Chu of E.Y. Laboratories of San Mateo, Calif. Laminin was prepared by R. Knibbs of this laboratory from a murine tumor (EHS sarcoma) as described in Shibata. AFGF-8 was obtained from Dr. C. A. Bush of the Illinois Institute of Technology, Chicago, Ill., α1-Acid glycoprotein and bovine testicular β-galactosidase as per Distler, were donated by Dr. G. W. Jourdian, University of Michigan.

Ovine submaxillary mucin, porcine submaxillary mucin, bovine submaxillary mucin, low molecular weight (about 10,500 daltons) antifreeze glycoprotein, and endo-α-N-acetylgalactosaminidase from *Streptococcus pneumoniae* were gifts of Dr. A. E. Eckhardt, Duke University. Exo-α-N-acetylgalactosaminidase (from chicken liver) was purchased from Genzyme Corporation (Boston, Mass.). Glycophorin and asialoglycopeptide $M_r$ Petryniak, J. Petryniak, B. Wasniowska, K., and Krotkiewski, H. (1980) *Eur. J. Biochem.* 105, 335–341 were gifts of Dr. J. Petryniak. Glycophorin also was isolated as described in, Drzeniek, Z., and Lisowska, E. (1979) *Arch. Immunol. Ther. Exp* 27, 253–262. Glycoproteins were desialylated in 0.1 N $H_2SO_4$ at 80° C. for 60 min. and desalted by dialysis. Glycophorin was desialylated as described in Petryniak, J., and Goldstein, I. J. (1986) *Biochemistry* 25, 2829–2838.

Methyl α-GalNAc, methyl β-GalNAc, and Galβ1, 3GlcNAcβ-$CH_2CH_2$=$CH_2$ were available in our laboratory at the University of Michigan. Galβ1,3GlcNAc was generated from the β-allyl derivative by acid hydrolysis in 20% acetic acid at 100° C. and subsequently isolated using a Bio-Gel P-2 column commercially available from Bio-Rad.

Purification of ACA was performed with a beginning supply of *A. caudatus* seeds having a mass of about 60 g. The seeds were finely ground and delipidated by extraction with methanol (200 ml×2) followed by $CH_2Cl_2$(200 ml×2). After air drying, the seed meal was extracted three times with 150 ml of phosphate buffered saline (PBS) at 4° C. for four to twelve hours. The three crude extracts were combined and made 30% saturated with $(NH_4)_2SO_4$ at 4° C., centrifuged, and the resulting pellet was discarded. Next, the supernatant fluid was made 80% saturated with $(NH_4)_2SO_4$ again at 4° C., the precipitate collected by centrifugation. After centrifugation the precipitated protein was dissolved in 150 ml of 20 mM trishydroxy-methyl-amino-ethane (Tris) having pH 8.1, and dialyzed extensively against the same buffer. After centrifugation to remove the insoluble material, the protein sample was applied to a DEAE-cellulose column (2.8×23 cm) which had been equilibrated with 20 mM Tris at pH 8.1. The protein fractions resulting from washing the column with 20 mM Tris, pH 8.1, were the only fractions which contained hemagglutinating activity. These fractions were pooled and applied to a Synsorb-T column (1.5×13 cm) equilibrated with PBS.

The unbound material was washed from the Synsorb-T beads with phosphate buffered saline (PBS), and the *A. caudatus* lectin was eluted with 0.1 N acetic acid, pH 3. The Synsorb-T beads are fine particles of diatomaceous earth, or sand material bonded to the disaccharide Galβ1,3GalNAcα-O—$(CH_2)_8CO$. The Synsorb-T column (1.5×13 cm) used had a capacity of approximately 50 mg of amaranthin. Thus, it was necessary to reapply the unbound material to the affinity column to obtain the remaining lectin.

CHARACTERIZATION OF THE AMARANTHIN

In the hemagglutination procedure, red blood cells were washed and resuspended to make a 2% suspension in phosphate buffered saline. The lectin solution was serially diluted in microliter plates followed by the addition of the 2% red blood cell suspension. Hemagglutination was observed after 1 hour at room temperature. One hemagglutination unit (HU) is defined as the minimum amount of amaranthin to completely agglutinate cells and is equivalent to a lectin concentration of 2 μg/ml. No difference was observed for the agglutination of type A, B, or O red blood cells.

Glycosidase digestions, and in particular exo-β-galactosidase digestions were carried out for 9 hours at 37° C. in 0.1 M sodium citrate, pH 4.3 using 0.1 unit of enzyme/μmol of terminal galactosyl group. Endo-α-N-acetylgalactosaminidase treatment of asialo-ovine submaxillary mucin was done as described in Sadler, J. E., Rearick, J. L., Paulson, J. C., and Hill, R. L. (1979). GSC Exo-α-N-acetylgalactosaminidase digestion of asialo-ovine submaxillary mucin was carried out according to the recommendations of Genzyme of Boston, Mass. Glycoproteins were analyzed for carbohydrate composition, before and after glycosidase treatment, as described.

Polyacrylamide gel electrophoresis was carried out according to Laemmll. Electrophoresis was performed in the presence of 0.1% SDS using a 12.5% slab gel. Native gel electrophoresis using a 7.5% slab gel was done at pH 4.3 according to Reisfeld et al. Protein bands were visualized by silver staining.

Precipitation assays were conducted in 1.5 ml centrifuge tubes by the method of So and Goldstein. Indicated amounts of glycoprotein were added to 80 μg of amaranthin, and the total volume was adjusted to 250 μl with phosphate buffered saline. The tubes were incubated at 37° C. and then kept at 4° C. for 2 days. The tubes were centrifuged, washed with cold Phosphate buffered saline, dissolved in 0.05 N NaOH and analyzed for protein by the method of Lowery et al. using bovine serum albumin as the standard. Hapten inhibition assays were carried out using 80 μg of amaranthin, 5 μg of asialo-ovine submaxillary mucins, and the indicated sugar concentrations. Inhibition was determined relative to the amount of precipitate formed in the control with no sugar added. All precipitation assays were conducted in duplicate to bring the tolerance within ±5% and the amount of precipitate formed average.

Precipitation reactions with PNA were carried out similarly, except that 40 μg of PNA was used. Hapten inhibition studies with PNA used 40 μg of PNA, 6 μg of asialoglycophorin, and the indicated sugar concentrations.

The pH dependence study utilized a 2-fold concentrate of a universal buffer system consisting of sodium citrate (24.6 mM), $KH_2PO_4$ (28.7 mM) sodium barbitol (29.1 mM), boric acid (28.8 mM), and NaCl (209 mM), and was adjusted to the indicated pH values with 0.2 N NaOH or 0.2 N HCl. Water was added to complete the 2-fold dilution and the pH was recorded. Amaranthin and asialo-ovine submaxillary mucin solutions were prepared as concentrated solutions in 0.9% NaCl. A standard precipitation assay with amaranthin (80μg) and asialo-ovine submaxillary mucin (5 μg) was carried out using the universal buffer at the indicated pH.

For metal analysis two methods were used to determine if metals were necessary for amaranthin activity. 1) Amaranthin was dialyzed against 1 N acetic acid at 4° C. overnight, and then against 20 mM phosphate buffer at pH 7.2. The acid dialyzed amaranthin was then used in the standard precipitation assay with asialo-ovine submaxillary mucin and the indicated additions. 2) After dialysis into metal free buffer, amaranthin was incubated for 1 hour at room temperature in the presence of the indicated ethylene diamine tetraacetate (EDTA) concentrations. Asialo-ovine submaxillary mucin was then added, and the precipitation assay was carried out as usual. All glassware was acid-washed and buffers were passed over a Chelex 100 column, a trademarked, column commercially available from Bio-Rad to remove divalent metal ions.

Native molecular weight was determined by gel filtration according to Andrews, P.(1964) *Biochem. J.* 91, 222–233. Filtration was performed using a Sephadex G-200 (superfine) column (1.5×98 cm) equilibrated with PBS at 4° C. The column was standardized with yeast alcohol dehydrogenase (of mass=150,000 daltons), bovine serum albumin (having a mass=66,000 daltons), ovalbumin (having a mass=45,000 daltons), soybean trypsein inhibitor (having a mass=20,100 daltons) and cytochrome c (having a mass= 12,400 daltons). Void and included volumes were determined with blue dextran 2,000 obtained from Pharmacia; Uppsala, Sweden, and $K_2CrO_4$ respectively, for each experiment.

Amino acid and carbohydrate analysis was performed. Amino acids were determined as previously described by Koop et al. Tryptophan was determined spectrophotometrically according to Edelhoch. Carbohydrate composition was analyzed as described by Perini and Peters.

TABLE I

Amaranthin purification summary
From 60-g A. caudatus seeds.

|   | Total Protein mg | Total Activity HU[a] | Specific Activity HU/mg | % Yield |
|---|---|---|---|---|
| 1) PBS extraction | 2,271 | 179,676 | 66 | 100 |
| 2) Ammonium sulfate precipitation | 1,006 | 161,890 | 161 | 90 |
| 3) DEAE-cellulose chromatography | 442 | 159,264 | 360 | 88 |
| 4) Synsorb-T chromatography | 101 | 100,900 | 999 | 56 |

[a]HU (hemagglutinating unit) = 2 μg amaranthin/ml was required to completely agglutinate cells.

Purification of amaranthin is summarized presented above in Table I. This method resulted in ACA which exceeded 90% 98% and 99% purity by weight Amaranthin represents about 3.7% of the total PBS-extractable protein from the seed meal, or 1.6–1.7 mg of amaranthin/gram of *A. caudatus* seeds. The lectin did not bind to the DEAE-ellulose resin in 20 mM Tris, pH 8.1, a finding which proved useful in the purification scheme since only one other protein was found to be present along with amaranthin in the pooled DEAE-cellulose fractions. When these pooled fractions were applied to the Synsorb-T column, the one contamination protein was washed from the column with PBS and the bound amaranthin subsequently eluted with 0.1 N acetic acid. Amaranthin was also isolated on fetuin-Sepharose, a less satisfactory adsorbent than Synsorb-T since rather harsh conditions were necessary to elute it from the fetuin-Sepharose resin (20 mM ethylenediamine, pH 11). In all respects, fetuin-Sepharose-purified lectin appeared identical to Synsorb-T purified lectin.

Elution of amaranthin from the affinity columns with non-specific agents was employed due to the expense and limited availability of Galβ1,3GalNAc, the best binding ligand. GalNAc (0.5 M) was effective in displacing amaranthin from the Synsorb-T matrix. However, when amaranthin (0.9 mg) was applied to a small Synsorb-T column (0.58 ml), it was observed that 100 μM Galβ1,3GalNAcα-O-benzyl eluted the lectin.

Molecular weight and homogeneity of amaranthin, using sodium dodecyl sulfate polyaczyiamide gel electrophoresis (SDS-PAGE) analysis of the Synsorb-T purified amaranthin, gave a single protein band (±βmercaptoethanol, not shown) with a subunit mass of 33,000–36,000 daltons. Native PAGE at pH 4.3 also gave a single protein band, a further indication that the amaranthin sample was homogeneous.

Gel filtration experiments indicated that, in PBS at 4° C., amaranthin had a mass of about 54,000 daltons. Subsequent measurements indicated a native mass closer to 63,000 daltons. FIG. 1 illustrates the gel filtration curve. The amount of amaranthin applied was varied in separate experiments from 1.6 to 14 mg. No change in molecular weight was observed when the Sephadex column was run in the presence of 100 mM glucose. Amaranthin always migrated as a single symmetric peak by gel filtration. The error involved in duplicate molecular weight determinations by gel filtration was ±5%.

TABLE II

Amino acid composition of amaranthin
Lectin was hydrolyzed in 6 N HCl (110° C. under $N^2$) and analyzed for amino acids as described. The composition of the lectin was calculated assuming a subunit mass of 36,000 daltons.

| Amino acid | Residues/molecule |
|---|---|
| Cys | 5.4[a] |
| Asx | 44.5 |
| Met | 5.7 |
| Thr | 16.1[b] |
| Ser | 32.8[b] |
| Glx | 30.6 |
| Pro | 11.5 |
| Gly | 30.2 |
| Ala | 13.3 |
| Val | 20.1 |
| Ile | 16.9 |
| Leu | 27.6 |
| Tyr | 17.0 |
| Phe | 17.0 |
| His | 7.0 |
| Lys | 21.9 |
| Arg | 10.6 |
| Trp | 9.0[c] |

[a]Determined as cysteic acid
[b]Determined by extrapolation to zero time hydrolysis.
[c]Determined spectrophotometrically as per Edelhoch, H. (1967) Biochemistry 6, 1948–1954.

TABLE 11A

| AMINO ACID COMPOSITION | RESIDUES PER MOLECULE |
|---|---|
| Cys | from about 5.1 to about 5.7 |
| Asx | from about 42.3 to about 46.7 |
| Met | from about 5.4 to about 6.0 |
| Thr | from about 15.3 to about 16.9 |
| Ser | from about 31.2 to about 34.4 |
| Glx | from about 29.1 to about 32.1 |
| Pro | from about 10.9 to about 12.1 |
| Gly | from about 28.7 to about 31.7 |
| Ala | from about 12.6 to about 14.0 |
| Val | from about 19.1 to about 21.1 |
| Ile | from about 16.1 to about 17.8 |
| Leu | from about 26.2 to about 29.0 |
| Tyr | from about 16.2 to about 17.9 |
| Phe | from about 16.2 to about 17.9 |
| His | from about 6.7 to about 7.4 |
| Lys | from about 20.8 to about 23.0 |
| Arg | from about 10.1 to about 11.1 |
| Trp | from about 8.6 to about 9.5 |

Amino acid composition and carbohydrate analysis were performed. The amino acid composition of amaranthin is presented in Table II. The amino acid composition and residues per molecule of a substantially pure homodimer lectin having a subunit mass of about 36,000 daltons is set forth in Table 2A. The lectin contains high amounts of acidic and hydroxy-amino acids and relatively large amounts of lysine, methionine, and tryptophan for a plant protein. The nutritional value of amaranth grain is due to its relatively high content of lysine and methionine, *Modern Prospects for an Ancient Crop.*; in this respect, it appears that amaranthin is similar to the overall amino acid composition of the cereal grains. Analysis of three separate preparations of amaranthin for covalently linked carbohydrate resulted in failure to detect the presence of any carbohydrate at the limits of sensitivity (i.e., ≦0.05 mol monosaccharide residues/mol lectin subunit). Attempts to sequence amaranthin revealed that the protein is blocked at its amino terminus in that it is inert to Edman degradation.

Figure 2:
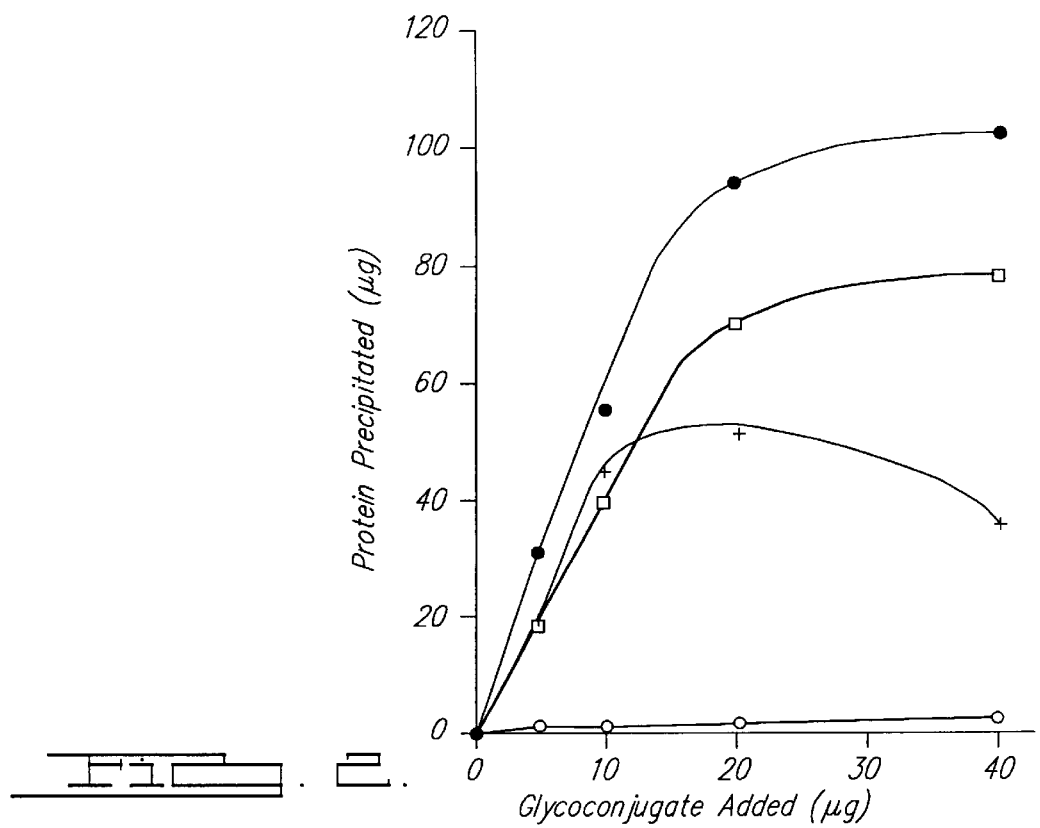
FIG. 2 is a graph illustrating the precipitation of ACA by glycoproteins.

The most active precipitating agent for amaranthin was asialoglycophorin as is shown in FIG. 2. In the graph of FIG. 2 each tube contained 80 μg of amaranthin. In FIG. 2, the diamond represents asialoglycophorin; the hollow diamond represents glycophorin; the hollow circle represents asialo-ovine submaxillary mucin; the hollow square represents porcine submaxillary mucin; the solid circle represents asialo-bovine submaxillary mucin; and X represents asialofetuin.

Native glycophorin appears to form a small amount of precipitate with amaranthin, but desialization of this glycoprotein resulted in a substantial enhancement of precipitation. Asialo-ovine submaxillary mucin also gave a significant precipitation reaction with amaranthin at low mucin concentrations. Asialofetuin, porcine submaxillary mucin, and asialo-bovine submaxillary mucin precipitated a small amount of amaranthin. Native bovine and ovine submaxillary mucins did not form precipitates. The synthetic glycoconjugates NeuAcα2,3Galβ1,3GalNAcα-OBSA,Galβ1,3[NeuAcα2,6]GalNAcα-O-BSA, and Galβ,3GalNAcα-O-BSA were also found to be good precipitating agents for amaranthin as will be shown in FIG. 4 below. All glycoproteins which precipitated amaranthin possess O-linked oligosaccharide structures. The following glycoproteins or glycoconjugates did not precipitate amaranthin: type A trisaccharide-BSA, p-azophenyl α- or β-GalNAc-BSA, laminin, asialo-α$_1$-acidglycoprotein, fetuin, hog gastric mucin (A+H), low molecular weight antifreeze glycoprotein having a mass of about 10,500 daltons, and antifreeze glycoprotein AFGP-8 having a mass of about 2,600 daltons.

Figure 3:
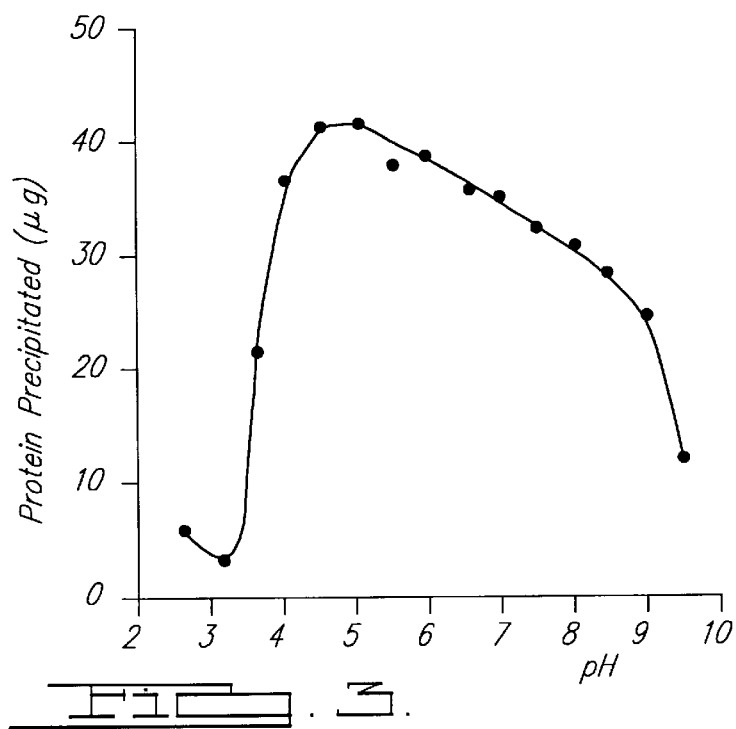
FIG. 3. is a graph of protein precipitation of ACA as a function of pH.

FIG. 3 shows the effect of pH on the amaranthin/asialo-ovine submaxillary mucin precipitation assay. Almost no precipitate formed at or below pH 3. Precipitation activity increased sharply between pH 3–4 and peaked at pH 5. Significant amaranthin activity was observed between pH 4–9.

TABLE III

Treatment of glycoproteins with glycosidases and subsequent amaranthin reactivity

| Glycoprotein | Glycosidase | % Sugar Released | Precipitate formation with amarantin |
|---|---|---|---|
| AOSM | (a) None | | Yes |
| | (b) Exo-α-N-acetyl-galactosaminidase | 90 | No |
| | (c) Endo-N-acetyl | —$^a$ | Yes |
| | (d) β-Galactosidase | —$^a$ | Yes |
| Asialo-glycopeptide M$_t$ | (a) None | | |
| | (b) β-Galactosidase | 60 | No |

TABLE III-continued

Treatment of glycoproteins with glycosidases and subsequent amaranthin reactivity

| Glycoprotein | Glycosidase | % Sugar Released | Precipitate formation with amarantin |
|---|---|---|---|
| Antifreeze glyco-protein, mass = 10,500 daltons | (a) None | | No |
| | (b) β-Galactosidase | 85 | No |

$^a$release was not monitored since galactose could not be detected for AOSM by our methods.

Selected glycoproteins were treated with glycosidases and used in the precipitation assay with amaranthin in an effort to determine the carbohydrate residues necessary for lectin interaction. Table III summarizes the results of these experiments, Antifreeze glycoprotein AFGP, as well as native or treated with β-galactosidase, did not precipitate with amaranthin. The asialoamino-terminal portion of glycophorin (asialo-glycopeptide M$_t$) reacted strongly with amaranthin, but its reactivity was eliminated upon release of 60% of its terminal galactosyl groups. When 90% of the GalNAc (GalNAcα-O-Ser/Thr) was released by α-N-acetylgalactosaminidase, AOSM failed to precipitate amaranthin. Two glycosidases, β-galactosidase or endo-N-acetylgalactosaminidase, were used to eliminate the small number of Galβ1,3GalNAcα-O-Ser/Thr residues from asialo-ovine submaxillary mucin. In each case, amaranthin reactivity was equivalent to untreated asialo-ovine submaxillary mucin.

TABLE IV

Effects of metals on amaranthin reactivity

| Condition | % Control reactivity$^a$ |
|---|---|
| 1) 5 mM EDTA | 100 |
| 2) 25 mM EDTA | 100 |
| 3) Acid dialyzed amaranthin & AOSM | 81 |
| (a) 0.1 mM CaCl$_2$ | 80 |
| (b) 0.1 mM MnCl$_2$ | 79 |
| (c) 0.1 mM MgCl$_2$ | 80 |

$^a$Control was 80 μg of amaranthin (untreated) plus 5 μg of asialo-ovine submaxillary mucin.

Table IV summarizes the experiments performed to determine the effect of metals on amaranthin activity. The presence of ethylene diamine tetra acetate (5–25 mM) had no effect on the precipitating activity of amaranthin. Acid-dialyzed amaranthin was 81% as active as untreated amaranthin. However, the addition of $CA^{2+}$, $Mn^{2+}$, or $Mg^{2+}$ did not restore the 20% loss in amaranthin activity. These data suggest that amaranthin does not have a metal requirement for activity.

Hapten inhibition of amaranthin/asialo-ovine submaxillary mucin precipitation was tested on the following saccharides: GalNac; GlcNAc; methyl N-acetyl-α-galactosaminide; methyl N-acetyl)-β-galactosaminide; methyl (2-O-acetyl)-a-galactoside; 3-O-(2-N-acetyl-α-D-galactopyranosyl)-N-(benzyloxycarbonyl)-L-serine methyl-ester; Galβ1,3GalNAc; Galβ1,3GalNAcα-O—CH$_2$CH=CH$_2$; Galβ1,3(2-acetamido-2-deoxy-1,5-anhydrogalactitol; Galβ1,3GalNAcα-O—(CH$_2$)$_8$COOCH$_3$; methyl (2-N-benzamido)-α-galactosaminide; methyl (2-N-p-nitrobenzamido)-α-galactosaminide; p-nitrophenyl N-acetyl α-galactosaminide; GalNAcα1,3Gal; GalNAcα1, 6Gal; GalNAcβ1,6Gal; Galβ1,3GalNAcα-O—CH₃; Glcβ1, 3GalNAcα-O—CH₃; Galβ1,3GalNAcα-O-benzyl; Galβ1,3 [6-F]GalNAcα-O,benzyl; GlcNAcβ1,3Galβ1,3GalNAcα-O-benzyl; AFGP-8(antifreeze glycoprotein having a mass of 2,600 daltons); and D-Fucβ1,3GalNAcα-O-benzyl.

Hapten inhibition studies seems to indicate that the best inhibitor of amaranthin/AOSM precipitation was Galβ3GalNAcα-O—R, where R was —OH, —CH₃, O-nitrophenyl, —(CH₂)₆COOCH₃, —CH₂CH=CH₂, or benzyl. This T-antigen disaccharide and its α-glycosides are 80 to 150 times more potent as inhibitors than GalNAcα-O—CH₃, which is the best monosaccharide inhibitor of amaranthin. In all cases active haptenic sugars completely inhibited precipitation. Table V tabulates all saccharides which were used as inhibitors of amaranthin and the respective concentration required for 50% inhibition of amaranthin/acyl-ovine submaxillary mucin precipitation. Since galactose, galactosamine, and Galβ1,3Galα-O—CH₃ are very poor inhibitors, it appears that the acetamido group in the C-2 position of GalNAc represents an important locus for lectin interaction. Glcβ1,3GalNAcα-O—Ch₃ is 10 times less potent than Galβ1,3GalNAcα-O—CH₃, indicating a preference for a C'-4 axial hydroxyl group in the galactosyl moiety. Galβ1,3GlcNAc was also a very poor inhibitor signifying that the C-4 hydroxyl group of the GalNAc unit must be in an axial position for good interaction with the lectin.

It also seems that the C-6 hydroxyl of the galactosyl group may not be important for lectin-binding since D-Fucβ1, 3GalNAcα-O-benzyl appears to be a very good inhibitor. It is interesting to note that substitution at the C-3 hydroxyl with an O-methyl group or NeuAc (NeuAcα2,3Galβ1, 3GalNAcα-O—(CH₂)₈-CO₂CH₃) does not decrease inhibitory potency; substitution at this point with GlcNAc (GlcNAcβ1,3Galβ1,3GalNAcaα-O-benzyl) decreases potency by a factor of 10. Therefore, C-3 hydroxyl group can be substituted without abolishing lectin binding. When the C-6 hydroxyl group of GalNAc is substituted by a fluorine atom (Galβ1,3[6-F]GalNAcα-O-benzyl), inhibition is equivalent to Galβ1,3GalNAca-O-benzyl indicating that the C-6 hydroxyl is either not involved in interaction with the lectin, or is not involved in the donation of a hydrogen atom for a hydrogen-bond interaction. Furthermore, since Galβ1,3[NeuAcα2,6]GalNAcα-O-BSA can precipitate amaranthin, it is evident that the C-6 hydroxyl of GalNAc can be substituted without destroying lectin binding. Thus, it appears that the C'-4 and C-4 hydroxyl groups, and the C-2 acetamido group of the T-antigen are the most important loci for interaction with amaranthin.

The α-anomer of the T-antigen disaccharide is preferred over the β-anomer. Table V shows that Galβ1,3GalNAcα-O—CH₂CH=CH₂ is 16-fold more potent than the anomeric Galβ1,3GalNAcαβ-O—CH₂CH=CH₂ as an inhibitor. The trisaccharide Galβ1,3GalNAcβ1,3Galβ-O—CH₃ was found to be a poor inhibitor. Finally, the fact that amaranthin can be precipitated by the Galβ1,3GalNAcα-O-BSA glycoconjugate, but not by the anomeric Galβ1,3GalNAcβ-O-BSA glycoconjugate, seems to indicate that the disaccharide must be in the α-anomeric configuration to interact significantly with amaranthin. Note that Galβ1,3(2-acetamido-2-deoxy-1,5-anhydrogalacitol), i.e. the 1-deoxy T-antigen, is only 1.7 times less potent than Galβ1,3GalNAc as an inhibitor. Therefore, it appears that the C-1 hydroxyl group is not involved in a direct binding interaction with amaranthin but rather that, when the disaccharide is linked β at its reducing terminus, it sterically interferes with the interaction of the disaccharide with the lectin-binding site.

Although AFGP-8 was unable to precipitate amaranthin, this glycoprotein was active as an inhibitor of amaranthin/ asialo-ovine submaxillary mucin precipitation. Considering the fact that this glycopeptide contains four T-antigen residues according to Rao, B. N. N., and Bush, C. A. (1987) *Biopolymers* 26, 1227–1244, a 50% inhibition value of 6 μM indicates that the AFGP-8 disaccharides are not able to interact with amaranthin as effectively as the free disaccharide.

Figure 4:
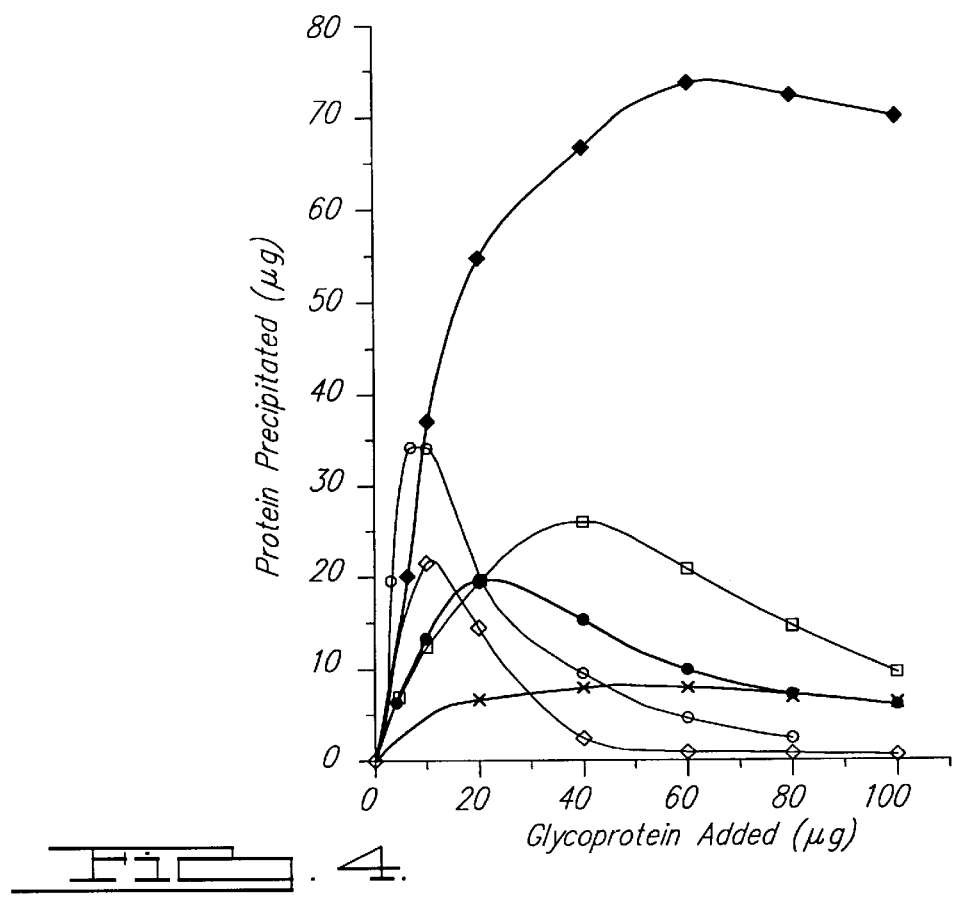
FIG. 4 is a graph of precipitation of ACA by bovine serum albumin (BSA) glycoconjugates.

In FIG. 4, precipitation of amaranthin by BSA-glycoconjugates as shown. Each tube contained 80 μg of amaranthin. The solid circle represents Galβ1,3GalNAcα-O-BSA; the hollow circle represents Galβ1,3GalNAcβ-O-BSA; the hollow square represents NeuAcα2,3Galβ1, 3GalNAcα-O-BSA; and the + represents Galβ1,3 [NeuAcα2,6]GalNAcα-O-BSA.

GalNAc, the only monosaccharide found to inhibit the amaranthin/asialo-ovine submaxillary mucin precipitation was 350 times less potent than Galβ1,3GalNAcα-O—R. In general, the requirements indicated above for the GalNAc moiety of the T-antigen disaccharide also apply to GalNAc itself. It is apparent that amaranthin can tolerate substitution at C-2 by the p-nitro-benzamido or benzamido group. Methyl (2-O-Acetyl)-α-galactoside is 8.6 times less potent than GalNAcα-O—CH₃. The α-anomer of GalNAc is preferred over the β-anomer for the methyl and p-nitrophenyl glycosides and for disaccharides terminating in GalNAc, (GalNAcα1,6Gal compared with GalNAcβ1,6Gal).

Figure 5:
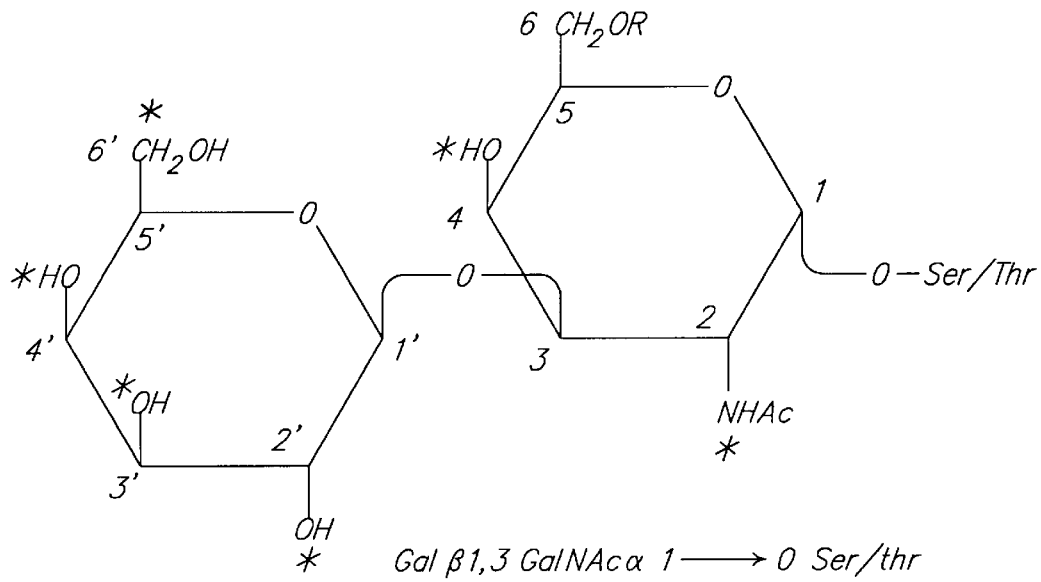
FIG. 5 illustrates a perspective view of the molecular model representing T-antigen/PNA interaction; and, FIG. 6 illustrates a perspective view of the molecular model representing T-antigen/ACA interaction.
Figure 6:
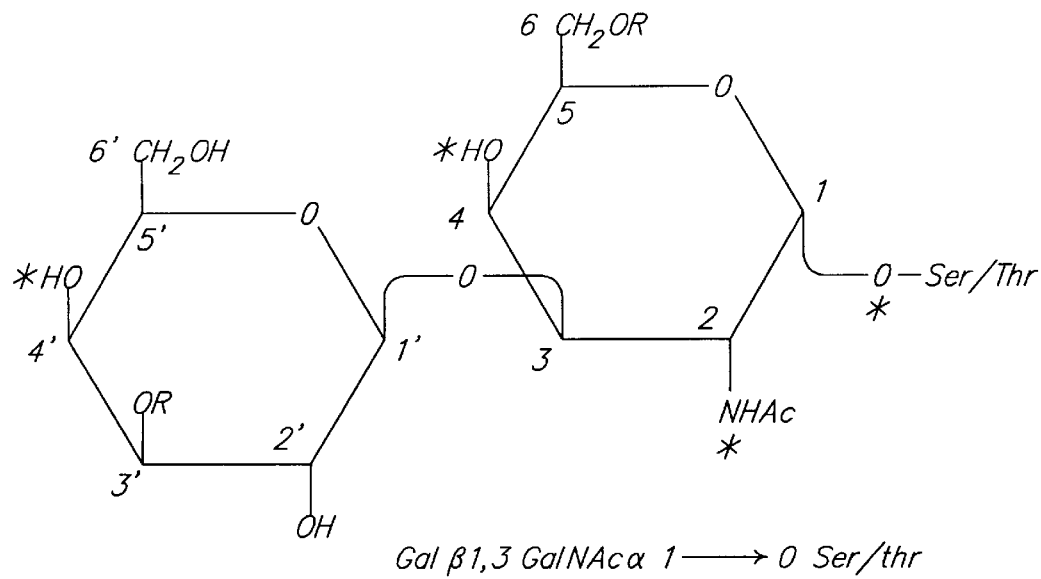

The Corey-Pauling-Koltan molecular models of T-antigen disaccharide were used as references for carbon location. The positions of the carbon atoms are labeled according to the appropriate numbering system. FIG. 5 illustrates a perspective view of the molecular model representing T-antigen/PNA interaction. FIG. 6 illustrates a perspective view of the molecular model representing T-antigen/ amaranthin interaction. The characterization results indicate that amaranthin has an extended carbohydrate-binding site which is specific for the T-antigen disaccharide, Galβ1, 3GalNAcα-O—R. It is apparent that the most important loci for lectin binding are the C'-4 hydroxyl group of the terminal galactosyl moiety and the C-4 hydroxyl group and C-2 acetamido group of the reducing GalNAc residue. From the space filling model of Galβ1,3GalNAc shown in FIG. 5, constructed according to the proton nuclear magnetic resonance data of Bush and Fenney (29), it is evident that the C'-4 and C-4 hydroxyl groups along with the C-2 acetamido substituent, constitute a well-defined constellation of surface features.

TABLE V

Inhibition of amaranthin/AOSM precipitation by saccharides

| Sugar | Amaranthin Conc. req. for 50% inhibition | Relative Inhibition potency | |
|---|---|---|---|
| | | ACA | PNA |
| N-Acetylgalactosamine | 0.79 | 1 | <0.4 |
| Galactosamine | 16% @ 500 | <0.002 | |
| Galactose | 13% @ 500 | <0.002 | 1 |
| D-Fucose | 6% @ 500 | <0.002 | |
| Glucose | 19% @ 500 | <0.002 | |
| N-Acetylglucosamine | 41% @ 500 | | |
| Methyl N-acetyl-α-galactosaminide | 0.25 | 3.2 | |
| Methyl N-acetyl-β-galactosaminide | 11.27 | 0.07 | |
| Methyl (2-N-p-nitrobenzamindo)-α-galactosaminide | 0.14 | 5.6 | |

TABLE V-continued

Inhibition of amaranthin/AOSM precipitation by saccharides

| Sugar | Amaranthin Conc. req. for 50% inhibition | Relative Inhibition potency | |
|---|---|---|---|
| | | ACA | PNA |
| Methyl (2-N-benzamido)-α-galactosaminide | 0.85 | 0.9 | |
| Methyl (2-O-p-nitrobenzoate)-α-galactoside | 31% @ 6 | <0.1 | |
| Methyl (2-O-acetyl)-α-galactoside | 2.14 | 0.4 | |
| Methyl (2-deoxy)-α-galactose | 0% @ 10 | <0.08 | |
| Methyl α-galactoside | 0% @ 250 | <0.003 | 2.2 |
| Methyl β-galactoside | 0% @ 250 | <0.003 | 0.8 |
| p-NitrophenylN-acetyl-α-galactosiminide | 0.45 | 1.8 | |
| p-NitrophenylN-acetyl-β-Zgalactosaminide | 0% @ 3 | <0.3 | |
| 3-O-(2-N-acetyl-α-D-galactopyranosyl-N-(benzyloxcarbonyl)-L-serine methyl ester | 0.053 | 15 | |
| GalNAcα1,3Gal | 0.31 | 2.5 | |
| GalNAcα1,6Gal | 0.21 | 3.8 | |
| GalNAcβ1,6Gal | 1.0 | 0.8 | |
| GalNAcα1,3GalNAcβ1-O(CH$_2$)$_6$Co$_2$CH$_3$ | 0% @ 0.9 | <0.9 | |
| Galβ1,3GalNAc | 0.0034 | 232 | |
| Galβ1,3GalNAcα-O-CH$_3$ | 0.0031 | 255-225- | 47 |
| Galβ1,3GalNAcα-O-o-nitrophenyl | 0.0021 | 376 | |
| Galβ1,3GalNAcα-O-CH$_2$-CH = CH$_2$ | 0.0021 | 376 | 38 |
| Galβ1,3GalNAcβ-O-CH$_2$-CH = CH$_2$ | 0.034 | 23 | |
| Galβ1,3GalNAcα-O-benzyl | 0.0016 | 494 | 50 |
| Galβ1,3GalNAcαO(CH$_2$)$_8$-CH-CH$_3$ | 0.0018 | 439 | 47 |
| Galβ1,3[6-F]GalNAcα-O-benzyl | 0.0017 | 465 | |
| 3-O-Methyl Galβ1,3GalNAcα-O-benzyl | 0.0020 | 395 | <10 |
| Galβ1,3(2-acetamido-2-deoxy-1,5-anhydrogalactitol) | 0.0058 | 136 | 14 |
| D-Fubcβ1,3GalNAcα-O-benzyl | 0.0019 | 416 | 11 |
| Galβ1,3Galα-O-CH$_3$ | 5% @ 1 | <0.8 | 4.2 |
| Gacβ1,3GalNAcα-O-CH$_3$ | 0.036 | 22 | |
| GlcNAcβ1,3[6-F]GalNAcα-O-benzyl | 6% @ 1 | <0.08 | |
| Galβ1,4Glc | 5% @ 75 | <0.01 | |
| Galβ1,4GlcNAc | 5% @ 100 | <0.008 | |
| Galβ1,3GlcNAC | 10% @ 10 | <0.08 | |
| Galβ1,3GlcNAcβ-O-CH$_2$—CH—CH$_2$ | 0% @ 10 | <0.08 | |
| Galα1,6Glc | 8% @ 100 | <0.008 | |
| Galβ1,3GalNAcβ1,3Galβ-O—CH$_3$ | 13% @ 1 | <0.08 | 38 |
| GlcNAcβ1,3Galβ1,3GalNAcα-O-benzyl | 0.025 | 32 | <10 |
| NeuAcα2,3Galβ1,3GalNAcα-O-(CH$_2$)$_8$—CO$_2$CH$_3$ | 0.0018 | 439 | |
| AFGP-8 | 0.006 | 132 | |

Thus it would appear that the amaranthin carbohydrate-binding site is complementary to these topographical features on the surface of the disaccharide. Furthermore, the disaccharide model illustrates that the C'-3, C'-6, and C-6 hydroxyl groups do not form part of the above indicated topography and thus it is reasonable that these hydroxyl groups are not important loci for amaranthin binding.

The pronounced preference for the α-anomer over the β-anomer of Galβ1,3GalNAc of FIG. 4 is probably steric in nature. From a space filing model (not shown), it would appear that when the disaccharide is in the α-anomeric configuration the anomeric hydroxyl (or substituent) is situated "away" from the putative amaranthin binding surface. However, when the disaccharide is in the β-anomeric configuration, the substituent C-1 moves into the putative amaranthin binding surface, creating steric hindrance to lectin binding.

The same concentration of sialylated T-antigen disaccharide (NeuAcα2,3Galβ1,3GalNAcα-O—(CH$_2$)$_8$CO$_2$CH$_3$) and Galβ1,3GalNAcα-O—(CH$_2$)$_8$CO$_2$CH$_3$ required for 50% inhibition of amaranthin/AOSM precipitation shown in Table V. The equivalent potency of these inhibitors suggests that the α2,3-linked NeuAc does not participate in the interactions with amaranthin, but rather, the C'-3-substituted NeuAc is oriented away from the putative binding surface recognized by the lectin. However, since NeuAcα2,3Galβ1,3GalNAcα-O (a cryptic T-antigen) is a naturally occurring O-linked trisaccharide, it is difficult to classify amaranthin simply as a T-antigen-specific lectin. Both Galβ1,3GalNAcαO-BSA and NeuAcα2,3Galβ1,3GalNAcαO-BSA have similar precipitation results with amaranthin as shown in FIG. 4, confirming that the C'-3 sialylated T-antigen also binds well to the lectin. It is also important to note that amaranthin can interact with GlcNAcβ1,3Galβ1,3GalNacα-O-Benzyl (Table V) reasonably well, further illustrating that the lectin is able to bind to the T-disaccharide even when it is not in a terminal position. Since none of the substituted T-disaccharides are better inhibitors of lectin precipitation than Galβ1,3GalNAcα-O, it is evident that the carbohydrate-binding site of amaranthin is complementary to the above defined hydroxyl and acetamido groups associated with the T-antigen By the use of molecular models constructed as predicted by hard-sphere exoanomeric calculations, it can be seen that the 2-acetamido group of the C-3 β-linked GlcNAc (GlcNAcβ1,3Galβ1,3GalNAcα-O-benzyl) can project toward the space adjacent to that delineated by O'-3, C'-3; and C'-2 of the penultimate galactose. The sialoside (NeuAcα2,3Galβ1,3GalNAcα-O), on the other hand does not offer similar steric hindrance to this space or surface adjacent to it. The carboxyl group of the sialoside projects away from the galactose ring roughly parallel to the C'4—O'4 bond of the galactose.

The C-3 methylene group of the sialoside is within the same view line as the acetamido group present in the GlcNAcβ1,3Gal residue relative to the penultimate galactose. These molecular modeling data may explain the 10-fold lower reactivity of GlcNAcβ1,3Galβ1,3GalNacα-O compared with NeuAcα2,3Galβ1,3GalNAcα-O. The sigma and psi angles used for the terminal glycosidic linkage of NeuAca2,3Galβ1,3GalNAcα were −165° and −15°. Sigma and psi angles for the GlcNAcβ1,3Galβ linkage were 60° and −10. It should be noted that psi can vary ±40° away from the value of −10° without dramatic increases in the energy of nonbonded interactions.

Inhibition by derivatives of GalNAc complements the results obtained for the T-antigen disaccharide. As indicated for the reducing GalNAc moiety of the disaccharide, important features for monosaccharide binding are an axial C-4 hydroxyl group, the C-2 acetamido, and a pronounced preference for the α-anomer.

Amaranthin readily forms a precipitate with glycoconjugates, containing Galβ1,3GalNAcα-O units and with glycoproteins except for the antifreeze glycoprotein. However, it was observed that amaranthin also precipitated asialo-ovine submaxillary mucin due to its large number of accessible GalNAcα-O-Ser/Thr residues. See Hill, Jr., H. D. Reynolds, J. A., and Hill, R. L. (1977) *J. Biol. Chem.* 252, 3791–3798 and Gerken, T. A. (1986) *Arch. Biochem. Biophysics* 247, 239–253. Although asialo-ovine submaxillary mucin has been reported to have very small amounts of Galβ1,3GalNAcα-O-Ser/Thr (0.5% of total carbohydrates), in experiments with β-galactosidase-treated or endo-N-acetylgalactosaminidase-treated asialo-ovine submaxillary mucin resulted in equivalent precipitin results for treated and untreated AOSM as shown in Table III. Therefore, amaranthin can also interact with the GalNAcα-O-Ser/Thr residues of AOSM. This interaction with terminal GalNAc would appear to be a special case since amaranthin does not bind to GalNAcα-Synsorb, or precipitate a p-azophenyl GalNAcα-BSA glycoconjugate. We have also observed that asialo-glycopeptide $M_t$, consisting of the $NH_2$-terminal 39 amino acids of asialoglycophorin, containing 12 Galβ1, 3GalNacα-O residues and one N-linked oligosaccharide reacts very well with amaranthin. This substance is reported by Petryniak. However, when 60% of the terminal galactosyl groups are removed from asialo-glycopeptide $M_t$, by β-galactosidase, amaranthin no longer precipitates this glycoprotein as shown in Table III. Thus, in general, amaranthin requires the T-antigen disaccharide for significant binding.

The observation that amaranthin binds tightly to fetuin-Sepharose is puzzling since the lectin does not precipitate fetuin. Each molecule of fetuin contains three O-linked oligosaccharide chains with the structure NeuAcα2,3Galβ1, 3GalNAcα-O-Ser/Thr or NeuAcα2,3Galβ1,3[NeuAcα2,6] GalNAcα-O-Ser/Thr. See Sprio, R. G. and Bhoyroo, V. D. (1974). *Biol. Chem.* 249, 5704–5717 and Nilsson, B. Norden, N. E., and Svensson, S. (1979) *J. Biol Chem.* 254, 4545–4553. Carbohydrate binding studies indicate that the lectin is able to bind certain sialylated derivatives of the T-antigen disaccharide and this may partially explain its ability to bind to fetuin-Sepharose. However, once bound, the lectin could not be eluted by buffers at pH 3 or 10.5, whereas, lectin bound to Synsorb-T is readily eluted by pH 3 buffer. These results suggest that amaranthin may interact with fetuin-Sepharose in a manner unrelated to the lectin's carbohydrate-binding properties and may be a characteristic associated with fetuin immobilized on Sepharose, e.g., binding may be due partially to interaction with the matrix and/or an off-rate which is substantially slower than the rate of elution from the column. Asialofetuin gives a weak precipitation reaction with amaranthin as seen in FIG. 3, indicating that the exposed T-antigen disaccharides of this glycoprotein can interact with the lectin. The presence of only 3 T-antigen disaccharide units/asialofetuin molecule as seen in the references above, may explain the small amount of precipitated protein compared with glycoproteins such as asialoglycophorin that are more highly substituted by T-antigen disaccharide units.

It is interesting to examine the difference between the binding specificities of the peanut (*Arachis hypogaea*) agglutinin, as reported by Lotan, R. Skutelsky, E., Danon, D., and Sharon, N. (1975) *J. Biol. Chem.* 250, 8518–8523 and Pereira, M. E., Kabvat, E. A., Lotan, R., and Sharon, N. (1976) *Carbohydr. Res.* 51, 107–118, with amaranthin. Although both lectins are most effectively inhibited by Galβ1,3GalNAc, the monosaccharide specificities of these lectins differ remarkably. Lotan reports PNA is inhibited by D-galactose but not by GalNAc, Lotan, whereas amaranthin is inhibited by GalNAc but not by galactose. PNA seems to react equally well with Galβ1,3GalNAcα-O-BSA and Galβ1,3GalNAcβ-O-BSA, indicating no anomeric preference of the disaccharide by PNA. Kaifu and Osawa also reported no anomeric preference for Galβ1,3GalNAc with PNA. Furthermore, PNA is precipitated by asialo-β$_1$-acid glycoprotein, reported by Pereira, which contains Galβ1, 4GlcNAc-terminal residues as in Fournet, B., Montreuil, J., Strecker, G., Dorland, L., Haverkamp, J., Viegenthart, J. F. G., Binette, J. P., and Schmid, K. (1978) *Biochemistry* 17, 5206–5214 and N-acetyllactosamine, as reported by Pereira, and Galβ1,3Galα-O—$CH_3$, shown in Table V to be rather good inhibitors. In contrast amaranthin is neither precipitated by asialo-α1-acid glycoprotein nor inhibited by N-acetylactosamine or Galβ1,3Galα-O—$CH_3$.

From these considerations, it appears that PNA recognizes the terminal galactose residue as the primary binding ligand, whereas amaranthin recognizes the internal GalNAc residue as its primary binding ligand. For each lectin the additional residue of the disaccharide increases the binding affinity by increasing the number of complementary interactions.

The difference in the primary site of binding between these two lectins offers a reasonable explanation for the fact that PNA reacts strongly with antifreeze glycoprotein, see Pereira, whereas amaranthin is nonreactive. The antifreeze glycoprotein consists of a repeating tripeptide sequence $(Ala-Thr-Ala)_n$, in which each threonyl residue contains the disaccharide unit Galβ1,3GalNAcα-O-, see reference Devries, A. L., Lp,atsi. S. L. and Feemeu, R. E. (1970) *J. Biol. Chem.* 245, 2901–2908 and DeVries, A. L., Vandenheede, J. A., and Feeney, R. E. (1971) *J. Biol. Chem.* 246, 305–308. Bush and Feeney, in Bush, C. A., and Feeney, R. E. (1986) *Int. J. Peptide Protein Res.* 28, 386–397 reported that the hydrophobic side of the disaccharide faces inward and interacts with the peptide backbone. Further, it is evident that in GalNAc, the methyl group of the acetamido moiety is in close proximity to the β-carbon atom of alanine. If, in fact, the 2-acetamido group is involved in interactions with the antifreeze glycoprotein (AFGP) peptide backbone, and given the fact that amaranthin has a strict requirement for this substituent, it is reasonable that amaranthin may not be able to interact with the disaccharide units of AFGP. In contrast, PNA recognizes primarily the terminal Gal of the disaccharide, which does not appear to be closely associated with the AFGP peptide backbone.

Inhibition studies have been performed with the antifreeze glycoprotein AFGP-8 to determine if amaranthin is capable of reacting with the T-antigen residues associated with AFGP. AFGP-8 is a 14-amino acid polypeptide which consists of alternating glycotripeptides of Ala-[Galβ1, 3GalNAcα-O]-Thr-Pro and Ala-[Galβ1,3GalNAcα-O]-Thr-Ala, with alanyl residues at amino and carboxyl termini, see Rao, B. N. N., and Bush, C. A. (1987) *Biopolymers* 26, 1227–1244, and Osuga, D. T., and Feeney, R. E. (1978) *J. Biol. Chem.* 253. 5338–5343. Even though AFGP-8 possesses four T-antigen disaccharides, it is 3-fold less potent as an inhibitor than the α-linked T-antigen disaccharides. Rao and Bush reported that the conformation of the disaccharides of AFGP-8 is very similar to other antifreeze glycoproteins. This inhibition data would support the above stated hypothesis that amaranthin cannot interact with the Galβ1, 3GalNAcα-O-Thr residues of AFGP effectively because of the lack of accessibility of the 2-acetamido group.

PNA does not agglutinate native A, B, or O red blood cells, see Lotan, whereas, amaranthin does. The PNA is not precipitated by NeuAcα2,3Galβ1,3GalNAcα-O-BSA. Similarly, Table V illustrates that substitution at the C'-3 position of galactose with either a methyl group or GlcNAc results in a significant decrease in inhibitory potency for PNA. NeuAcα2,3Galβ1,3GalNAcα-O-Ser/Thr is present as an oligosaccharide consisting of glycophorin as reported in Thomas, D. B., and Winzler, R. J. (1969) *J. Biol Chem.* 244, 5943–5946, a major component of red blood cell membranes. Thus, the difference described for the relative importance of the C'-3 hydroxyl of galactose for PNA and amaranthin readily explains the contrast found for the agglutination of red blood cells.

The preliminary experiments to determine if amaranthin requires divalent cations for activity indicated that metals were not necessary. Similarly, Zenteno and Ochoa, in Zenteno, see above, reported that the hemagglutinating activity of the *A. leucocarpus* lectin activity did not change in the presence or absence of divalent metals. In contrast, PNA contains 1 mol each of $Ca^{2+}$ and $Mg^{2+}$/mol of PNA subunit, see Neurohr, K. J., Young, N. M., and Mantsch, H. H. (1980) *J. Biol. Chem.* 255, 9205–9209.

The *Amaranthus leucocarpus* lectin is similar to amaranthin in several respects, including: both lectins agglutinate A, B, and O red blood cells equally well, interact with fetuin, are inhibited by GalNAc, and do not appear to require divalent cations for activity. These two lectins from Amaranthus also exhibit some notable differences. *Amaranthus leucocarpus* was reported to be a glycoprotein which was mitogenic to mouse spleen lymphocytes, and amaranthin does not contain covalently linked carbohydrate and is reported to be non-mitogenic to hog lymphocytes, see Pardoe. Further analysis of the *A. leucocarpus* lectin carbohydrate-binding site is needed before additional comparisons with amaranthin can be made. The purification method for amaranthin is equally effective for lectins for all amaranthus genuses, including leucocarpus and cruentus in addition to caudatus.

The *A. cruentus* is also best inhibited by GalNac and fetuin and is immunochemically related to crude extracts of *Amaranthus caudatus* seeds, see Koeppe. It appears that amaranthin and the *Amaranthus cruentus* lectin may be very similar with the possible exception that the *Amaranthus cruentus* lectin contains 2.2% neutral sugars.

Another T-antigen-specific lectin, present in Artocarpus intergrifolia seeds, was described by Sastry et al., see Sastry, M. V. K., Banarjee, P., Patanjali, S. R., Swamy, M. J., Swarnalatha, G. V., and Surolia, A. (1986) *J. Biol. Chem.* 11726–11733. This lectin binds galactose, galactoamine, and GalNAc with approximately the same affinity. Gal$\beta$1,3GalNac is 100 and 37 times more potent than galactose and GalNAc, respectively, indicating that the *Artocarpus lectin* also has an extended binding site. The *Artocarpus lectin* does not bind Gal$\beta$1,4GlcNAc or Gal$\beta$1,3GlcNAc, see Sastry. These results are similar to the results given above for amaranthin.

By using the lower limit of the subunit mass of 33,000 daltons, it originally appeared that amaranthin migrated by gel filtration with a native molecular weight relatively close to the expected 66,000 for a homodimer. Subsequently, the mass was found to be about 63,500 daltons. The earlier determined lower than expected native molecular weight did not result from lectin interactions with the cross-linked dextran, since amaranthin native molecular weight was unchanged in the presence of glucose. It is likely that the discrepancy between the observed and expected native molecular weights can be explained by differences in the shape of amaranthin and the proteins used to standardize the gel filtration column.

MEDICAL RESULTS

On the basis of our studies, we believe amaranthin will prove to be a reliable, valuable, highly specific probe for the T-and cryptic T-antigen.

ACA has a subunit molecular weight of approximately 33,000 daltons and exists as a homodimer having a native mass of 63,500 daltons with one binding site per monomer. ACA selectively binds the T antigen and variants thereof in proliferating colorectal epithelium, but interacts through different hydroxyl groups than does the closely related PNA lectin from the peanut, and therefore, has a slightly different binding specificity to synthetic oligosaccharide structures. The lectin has been conjugated to biotin, and has been used with an avidin-peroxidase complex to perform lectin histochemistry on specimens of human colon.

Using specimens of normal human colon, free of neoplasia, obtained at "instant autopsies", ACA bound to glycoconjugates in the lower half of 46±4% of colonic crypts, compared with the upper half of 7±2% of colonic crypts (n=23, p<001). ACA has a high affinity for glycoconjugates of colon cancers, and bound to 97±2% of the malignant glands in 13 adenocarcinomas of the colon.

Similarly, ACA bound to 82±7% of the glands in 6 adenomatous polyps. A total of 28 specimens of colonic tissue from 12 patients with familial polyposis coli were studied histochemically using ACA. The lectin bound to the glycoconjugates in a mean of 67±6% of the epithelial glands. When the tissue were analyzed for histopathology, a mean of 83±7% of glands in polypoid tissues were labeled compared with 60±7% of glands in the flat mucosa from familial polyposis coli (p=0.055).

A solid phase enzyme-linked lectin-binding assay has been developed for ACA to quantitate lectin binding to solubilized glycoconjugates. ACA is more sensitive in the measurement of purified cancer-associated mucin than peanut lectin, and can detect as little as 1 mg of mucin purified from the LS174T xenograft.

TISSUE PROCUREMENT

Specimens of adenocarcinoma of the colon and adenomatious colonic polyps from resected specimens were obtained from the Pathology Service at the Ann Arbor Veterans Administration Medical Center. These specimens were obtained at surgery or at colonoscopic polypectomy, fixed in buffered formalin, and embedded in paraffin for routine pathological examination. Additional four micron sections were cut for lectin histochemistry after the pathological diagnosis was confirmed.

Full-thickness specimens of normal colonic epithelium were obtained from the "Immediate Autopsy" program at the University of Maryland Human Tissue Resource or Johns Hopkins Research (JHR). These tissues came from accident victims with no pathological abnormality of the colon, were immediately fixed in formalin after death, and embedded in paraffin and sectioned for lectin histochemistry.

Full thickness specimens of colonic tissue were obtained from colectomy specimens for familial adenomatous polyposis at Johns Hopkins Hospital, fixed in formalin, and embedded in paraffin for tissue sectioning. The tissue specimens contained normal-appearing flat mucosa familial adenomatous polyposis, or FAP-normal, as well as a polypoid, adenomatious tissue familial adenomatous polyposis, or FAP-abnormal.

Rectal biopsies were obtained from individuals who were first degree relatives of patients with hereditary nonpolyposis colorectal cancer (HNPCC) as identified by H. T. Lynch, M.D. These patients were the siblings or offspring of index patients who fit the criteria for Lynch Syndrome I or II. See Drzeniek, Z., and Usowska, E. (1979) *Arch. Immunol Ther. Exp.* 27, 253–262. However, since there is no definitive genetic or phenotypic marker for this familial syndrome, it is not possible to be certain that these patients represent a single homogenous genetic abnormality. The biopsies were fixed in formalin, and embedded in paraffin for tissue sectioning.

LECTIN HISTOCHEMISTRY

Four micron paraffin embedded tissue sections attached to glass slides were deparaffinized by serial incubations in xylene (twice), absolute ethanol (thrice), 95% ethanol, 70% ethanol, water and finally equilibrated in phosphate buffered saline (PBS), pH 7.0, containing 0.1% bovine serum albumin (BSA) commercially available from Sigma Corp of St. Louis, Mo. The slides were blotted dry adjacent to the tissue sections, and biotinylated lectin was added at a concentration of 10 µg/ml (for ACA) and 20 µg/ml (for PNA) in a quantity sufficient to completely cover the hydrated tissue (100–2001 µl). The lectin was rinsed off after a 30 minute incubation by eight 2-second dips into phosphate buffered saline. The slides were again blotted, and the tissue covered with Streptavidin-horseradish peroxidase (HRP) obtained from Zymed Laboratories, San Francisco, Calif. at a concentration of 10 µg/ml for 30 minutes. The slides were rinsed as mentioned above, and the pigmented reaction product developed by the addition of a freshly prepared chromogen reagent solution prepared within two hours of use as follows.

3,3'-diaminobenzidine was aliqotted at 5 mg/mL in 0.01 M (Tris) tris hydroxy methyl amino methane saline, pH 7.5 and frozen at −70° C. until use. For use, the aliquot was thawed, diluted 1:10 in 0.01 M (Tris) tris hydroxy methyl amino methane saline pH 7.5, and 3.3 µL of 30% $H_2O_2$ were added to each 5 ml. This solution was allowed to stand for 10 min, and 100–200 µl was applied to the tissue sections that had been incubated earlier with biotinylated lectin and Streptavidin-HRP. After 10 min, the slides were rinsed with albumin-free phosphate buffered saline. The tissues were briefly counterstained for 50 seconds with Gill's #3 hematoxylin bovine serum albumin, commercially available from Sigma Corp. of St. Louis, Mo., rinsed with water, and serially dehydrated using graded alcohols and xylene, and embedded in Permount, a trademarked, commercially available product of Allied-Fischer Scientific of Livonia, Mich.

The specificity of lectin binding was evaluated by preincubating the biotinylated lectin with inhibitory hapten sugar for 1–2 hours prior to its application to the tissue. In each instance, the reagents were prepared so that the final concentration of lectin on the slide was either 10 or 20 µg/ml and the hapten sugar was as indicated in the results. Galactose, lactose, GalNAc, and galactose-β1-3N-acetylgalactosamine-α-O-benzyl (T-antigen-α-O-benzyl) were also obtained from Sigma Corp.

Sialidase digestions were performed on the tissue sections after hydration. Vibrio cholerae neuraminidase, also commercially available from Sigma Corp. of St. Louis, Mo. was diluted in 50 mM citrate-phosphate buffer, pH 4.5, at a concentration of 0.43 µU/ml, and 100–200 µl were incubated on the slide at 37° C. for 16 hours. Newcastle disease virus neuraminidase (viral suspension, U.S. Dept. of Agriculture, Agriculture Research Service, Athens, Ga.), was diluted in 50 mM cacodylate buffer, pH 6.0, at a concentration of 0.5 mU/ml, and 100–200 µl was added to the tissue for a 22 hours incubation at 37° C. Controls for these experiments utilized the same buffers without neuraminidase.

SCORING THE TISSUE SECTIONS

The stained sections were examined with a light microscope using a 25× and 40× objective lenses and 10× eyepiece. Evaluation of lectin binding required the use of several approaches. First, the binding specificity was confirmed by coincubation of lectin with hapten sugars known to bind the lectin maximally. Maximum labeling of the brown reaction product was arbitrarily assigned a score $4^+$. See Boland, C. R., Bresalier, R. S., and Roberts, J. A. "Assay of lectin binding sites in colonic cancer-associated mucins: comparison of fluorescence microscopy with a quantitative chromatographic technique." J. Histochem. Cytochem., 36: 1329–1334, 1988. No staining of the slide compared to control sections (i.e., in which lectin was omitted from the staining procedure) was assigned a score of 0. Intermediate scores of $1^+$ (trace or weak staining definitely not seen on control slides) and $2+3^+$ (stronger staining, but definitely less than maximal) were assigned. Although subjective, the histochemical scoring system using lectins has been demonstrated to correlate well with an objective measure of the binding of lectins to glycoproteins extracted from colonic tumors. See Boland. This method was used to confirm the binding specificity to known "positive" tissues and to evaluate changes in lectin binding after neuraminidase treatment.

A second method for scoring tissues was used to survey normal colonic tissues, adenomatous polyps, and cancers. For these studies, individual epithelial "units" were counted as either positive or negative; i.e., each crypt of Lieberkühn or neoplastic gland was considered an independent scorable unit, and the tissue score was expressed in terms of the percentage of units with any degree of definite labeling as from $1^+$ to $4^+$. The normal colonic crypt was further subdivided into the lower half and upper half for independent scoring because of the non-uniform distribution of labeling between the proliferative region (at the base), and the region of mature, differentiated cells (at the top).

Finally, an examination of the HNPCC tissues revealed subtle variations in labeling that required a more sophisticated method of scoring. These tissues were histologically normal, but showed variations in intensity of labeling when compared to the normal colonic tissues. Therefore, each individual crypt of Lieberkühn was given a score from $0-4^+$, and the labeling was expressed as a "weighted average", or, the sum of scores from 100 crypts, which could range from 0 (all crypts not labeled) to 400 (all 100 crypts maximally labeled). A modification of this approach has been used to evaluate histochemical results using other lectins, and provides reproducible scores on tissue sections as reported in Sams, J. S., Lynch, H. T., Burt, R. W., Lanspa, S., and Boland, C. R. "Abnormalities of lectin histochemistry in familial polyposis coli and hereditary nonpolyposis colorectal cancer," Cancer (in press), 1990.

RESULTS OF TISSUE TESTS

Lectin-Binding Specificity

Specimens of well differentiated colonic cancers were incubated with biotinylated lectins. Working concentrations on the slide were 10 µg/ml for ACA and 20 µg/ml for PNA. The hapten sugars galactose (Gal), N-acetylgalactosamine (GalNAc), and Galβ1,3GalNAc-α-O-benzyl (T-antigen) were used to inhibit lectin binding to the tissues. Using the biotinylated lectins, ACA produced intense labeling on most colon cancers. For purpose of the inhibition studies the scores were recorded from 0 to $3^+$ since the cancers were uniformly labeled and since a simplified scoring system was most useful. Glycoconjugates secreted into the malignant glands or lumens were the predominant location of labeling. Cytoplasmic labeling was less intense in all specimens. Biotinylated PNA labeled these tissues much less intensely, and was given a relative score of $1^+-2^+$ on the fifteen cancer specimens as the maximal degree of labeling. The ability of hapten sugars to inhibit labeling with these lectins is indicated in Table IV.

Labeling by ACA was inhibited by concentrations ≧250 mM GalNAc, and ≧100 µM T-antigen, but required 400 mM lactose or galactose for partial inhibition of binding. PNA was inhibited by ≧10 mM galactose, or lactose, ≧100 µM T-antigen, and ≧100 mM GalNAc.

TABLE VI

| | | Inhibitory hapten sugars | | | | | | | | | | | | | |
|---|---|---|---|---|---|---|---|---|---|---|---|---|---|---|---|
| | | T-antigen (μM) | | | GalNAc (mM) | | | | | Gal (mM) | | | Lactose (mM) | | |
| Lectin | None | 100 | 200 | 400 | 2.5 | 10 | 20 | 100 | 250 | 2.5 | 10 | 20 | 100 | 400 | 200 | 400 |
| ACA (10 μg/ml) | 3+ | 0 | 0 | 0 | 3+ | 3+ | 3+ | 1+ | Trace | 3+ | 3+ | 3+ | 3+ | 2+ | 2–3+ | 1–2+ |
| PNA (20 μg/ml) | 1–2+ | 0 | 0 | 0 | 1–2+ | 1–2+ | 1–2+ | 0 | 0 | Trace | 0 | 0 | 0 | 0 | 0 | 0 |

Legend:
Inhibition of lectin binding with hapten sugars on well differentiated colonic adenocarcinoma sections. Labeling was scored on a simplified scale from 0–3+ for this experiment, as described in the Methods.

Survey of Tissue Labeling with ACA

Lectin histochemistry was analyzed with biotinylated ACA, and tissue labeling was expressed in terms of the percentage of epithelial units showing any degree of definite reaction product from $1^+$–$4^+$.

Normal Colon

Twenty-three specimens of normal colon were obtained from sixteen "immediate autopsy" cases, and were free of histological abnormality. Full thickness, well-oriented sections were available in each case. Initial examination of these tissues indicated that ACA labeling was faint ($1^+$ for most specimens), and preferentially occurred at the base of the crypt of Lieberkühn in the apical cytoplasmic region, microvillar membrane, and glycocalyx, but was less frequently seen in the upper half of the crypt, which occurred in only 2/16 of the normal colons. Goblet cell mucin, connective tissue and lamina propria were not stained. The epithelial crypt unit was evaluated separately for staining of the base or lower half and upper half of the crypt. Labeling was seen in the lower half, or base of the crypt in all colonic specimens, and was present in 46%±4% of all crypts in the 23 specimens studied. The upper half of the crypts showed staining in 7%±2% of all crypts, and consisted of secreted material in the lumen of the gland in some cases, but definitely labeled ($1^+$–$2^+$) in the apical membrane and cytoplasm in 2/23 of the specimens. In these two cases, >30% of the epithelial units had $1^+$–$2^+$ labeling. The difference in labeling between upper and lower crypt regions was statistically significant ($p<0.001$). More importantly however, 18/23 normal colonic specimens showed no labeling in the upper portion of the crypt.

No labeling of mucosal glycoconjugates in the normal colon was observed with PNA. Treatment with *V. cholera* or Newcastle Disease virus neuraminidase for 16 hours did not produce an increase in labeling by PNA.

Neoplastic Colon

Twenty-five specimens of colonic adenocarcinoma were studied with ACA, and fifteen specimens with PNA. In all cases, labeling by ACA was more intense and more diffusely distributed than that seen with PNA, which was weaker in intensity, generally localized to secreted material, and focal within most of the tumors. Labeling of cytoplasmic glycoconjugates was commonly seen with ACA. Every cancer specimen showed extensive labeling with ACA, and in a limited study of 13 cancer specimens 97%±2% of the malignant glands showed $1^+$ to $3^+$ labeling of the secreted or cytoplasmic glycoconjugates. This was significantly greater than that seen in the normal colon ($p<0.001$).

Cancer specimens were digested with neuraminidases from *V. cholerae* (which hydrolyzes both α2,3 and α2,6-linked sialic acid [Neu5Ac]), and Newcastle disease virus (which preferentially hydrolyzes α2,3-linked Neu5Ac). See Corfield, P., Wember, M., Schauer, R., and Rott, R. The specificity of viral sialidases—the use of oligosaccharide substrates to probe enzymic characteristics and strain-specific differences. *Eur. J. Biochem.*, 124: 521–525, 1982 and, Goldstein I. J., Poretz, R. D. Isolation, physiochemical characterization, and carbohydrate binding specificity of lectins. In: I. E. Liener, N. Sharon, and I. J. Goldstein (eds.) *The Lectins. Properties, Functions and Applications in Biology and Medicine*, Chapter 2, pp 33–247, Orlando, Fla., Academic Press, Inc., 1984. Treatment with *V. Cholerae* neuraminidase greatly enhanced the intensity and distribution of PNA binding, exposing binding sites in secreted and cytoplasmic glycoconjugates. However, the use of Newcastle disease virus neuraminidase had much less effect on the intensity of labeling by PNA. Both enzymes enhanced PNA staining in connective tissue. Neither sialidase enhanced labeling with ACA.

The mucosa immediately adjacent to colonic cancer, called "transitional mucosa", is known to express abnormal glycoconjugates in spite of its non-neoplastic pathological appearance Boland, C. R., Montgomery, C. K., and Kim, Y. S., "Alterations in Human Colonic Mucin Occurring with Cellular Differentiation and Malignant Transformation," *Proc. Nati. Acad. Sci., U.S.A.* 79: 2051–2055, 1982. This mucosa demonstrated $1^+$ labeling in the upper and lower crypt region using ACA. Of interest, the collagen, blood vessels and muscle surrounding invasive cancers were variably labeled in 22/25 tumors, which was never seen in surrounding normal colonic epithelium.

A small group of six adenomatous polyps was studied using ACA. The lectin bound to 82%±7% of the glands in the adenomatous polyps, and stained cytoplasmic as well as secreted glycoconjugates. A larger group of adenomatous polyps confirms this observation.

Familial Adenomatious Polyposis (FAP)

A total of 28 specimens of colonic tissue from 12 patients with FAP were examined with ACA. Each specimen contained flat, normal-appearing epithelium and small adenomatous polyps. Epithelial units from flat and polypoid tissue were scored separately. Polyploid tissues demonstrated labeling in 83%±7% of the glands, which is similar to that seen in the small series of sporadic adenomatous polyps, all of which were larger than those present in the FAP sections. The flat tissue in FAP demonstrated labeling in 60%±7% of the glands ($p=0.055$ compared with polypoid tissue), and labeling was inappropriately seen in the upper portion of the crypt as frequently as in the lower portion. Labeling in FAP tissues was significantly greater than that seen at the apical portion of the crypt in normal colons ($p<0.001$), but was not different from that at the basal portion of the crypt ($0.05<p<0.10$), however, the intensity of labeling was greater in FAP sections in all portions of the crypt. Secreted glycoconjugates demonstrated an increase in staining intensity. The histochemical results are summarized in Table VII.

TABLE VII

Summary of ACA Histochemistry I

| TISSUE | Percent of Epithelial Units Labeled |
|---|---|
| Normal colonic epithelium (N = 23) | |
| upper half of crypt | 7 ± 2% |
| lower half of crypt | 46 ± 4% |
| Well differentiated colonic cancer (N = 25) | 97 ± 2% |
| Adenomatious colonic polyps (N = 6) | 82 + 7% |
| Familial adenomatous polyposis (N = 28) | |
| flat tissue | 60 ± 7% |
| polypoid tissue | 83 ± 7% |

Legend:
The percentage of epithelia units showing any definite lectin labeling is expressed as the mean ± SEM.

Hereditary Nonpolyposis Colorectal Cancer

Hereditary nonpolyposis colorectal cancer (HNPCC) is a more problematic tissue to evaluate. Rectal biopsies were obtained from individuals at risk for this syndrome, but no markers have been available to definitively identify truly affected patients. These tissues were all histologically normal, and lectin staining was scored from 0° to 4° using the "weighted average" method. An examination of the HNPCC tissues revealed that a subset exhibited an inappropriate increase in labeling with ACA (compared with colonic tissues from the Immediate Autopsy Program) both an increase in intensity and labeling of the cytoplasm in both the upper and lower portions of the crypt. For these tissues, each crypt was considered an independent "unit," and scored regardless of the cellular location within the crypt.

The weighted average for normal colon was 65±33. The score for HNPCC tissues was 74±70 (p<0.05 compared with normal colon). However, it was apparent that the HNPCC scores were not uniformly distributed, and contained a group of outliers with high scores. Five of the group had a score of 203±43 (p<0.001 compared with normal colon). When 11 of the FAP tissues were scored in this manner, a weighted average of 224±76 was obtained, which is p<0.001 compared with normal colon, which was not different from that seen in the HNPCC outliers as is shown in Table VIII.

TABLE VIII

Summary of ACA Histochemistry II

| Tissue | Weighted Average (0–400) |
|---|---|
| Normal colon (N = 14) | 65 ± 33 |
| HNPCC (N = 32) | 74 ± 70* |
| HNPCC outliers (N = 5) | 203 ± 43** |
| FAP (N = 11) | 224 ± 76** |

Legend:
The weighted average is a sum of labeling scores, each of which ranges from 0–4, for 100 epithelial units in the tissue. The scores, which can range from 0 (all units = 0) to 400 (all units = 4+), are expressed as mean ± SEM.
*Indicates a significate difference from normal colon, p < 0.05.
**Indicates a significant difference from normal colon, p < 0.001.

DIRECT COMPARISON OF BIOTINYLATED ACA AND PNA

Since prior work with PNA on familial colon cancer had been undertaken using the fluorescein-conjugated lectin as in Sams, we compared biotinylated ACA and PNA on paired sections, using the simplified, global 0–3$^+$ scoring system as was used for hapten sugar inhibition studies in Table IV. This experiment demonstrated that biotinylated PNA does not bind to normal or FAP colonic tissues, rarely binds to HNPCC, and binds 1–3$^+$ in colon cancers, as demonstrated in Table IX.

TABLE IX

Comparison of biotinylated ACA and PNA on human colonic tissues

| Tissue | N = | ACA Staining | PNA Staining |
|---|---|---|---|
| Normal colon | 6 | 1$^+$ | 0 |
| HNPCC | 19 | 1$^+$(17) | 0(17) |
| | | 2–3$^+$ | 1$^+$ |
| FAP | 7 | 2–3+ | 0 |
| Colon Cancer | 15 | 3$^+$ | 1–2$^+$14 |
| | | | 3$^+$(1) |

Legend:
Tissues stained with biotinylated ACA (10 μg/mL) or PNA (20 μg/mL) and scored from 0–3+ using the global assessment as described in the Methods.

DISCUSSION

In general, ACA is a newly isolated, T-antigen binding lectin adapted for histochemical studies of colorectal neoplasia. Data obtained during the characterization of the lectin suggested that its recognition specificity might differ from that of PNA, another lectin that binds T-antigen *Modern Prospects for an Ancient Crop*. ACA has unique tissue labeling characteristics compared to PNA, which suggests that variable forms of T-antigen may be produced in the colon under different biological circumstances. Lectins are particularly valuable as histochemical probes because of their ability to generate a reliable and uniform preparation of a stable agglutinin, the possibility for documentation of binding specificity with a high degree of precision, and their use on formalin fixed, paraffin embedded, tissue sections. (Rinderle, S. J., Goldstein, I. J., Matta, K. L., and Ratcliffe, R. M. *J.Biol. Chem.*, 264: 16123–16131, 1989.

The most important and novel aspect of ACA histochemistry was its ability to bind to epithelial cell glycoconjugates at the basal portion of the crypt of Lieberkühn, the proliferative zone in normal colonic mucosa. Labeling preferentially occurs in cytoplasmic, mucin-type glycoconjugates (although not necessarily mucins per se), on the apical membranes, and in secretions at the base of the colonic crypt, but is typically not expressed as the cells mature and migrate toward the lumenal surface of the epithelium. In a smaller number of specimens, labeling also was seen in the upper portions of the colonic crypt, but this was exceptional. We have previously reported that β-linked galactosyl residues are preferentially expressed in goblet cell mucins from the lower half of the colonic crypt using *Bauhinea purpurea* agglutinin (BPA) and *Ricinis communis* agglutinin$_1$ (RCA$_1$). See Boland. A major limitation of these two lectins is that their binding specificity is relatively broad, and epithelial cell glycoconjugates are labeled by both lectins throughout the colonic crypt, limiting their utility to further identify proliferation-associated structures. ACA has a more restricted range of labeling in the colon, but shares with BPA and RCA preferential binding to glycoconjugates in the lower half, or proliferative region of the colonic crypt. This occurs in spite of the apparent paradox that BPA and RCA bind to cytoplasmic and secreted glycoconjugates possessing terminal galactosyl residues Yuan, M., Itzkowitz, S. H., Boland, C. R., Kim, Y. D., Tomita, J. T., Palekar, A., Bennington, J. L., Trump, B. F., and Kim, Y. S. *Cancer Res.*, 46: 4841–4847, 1986. Whereas ACA is a T-antigen binding lectin that has a critical interaction with GalNAc. See Rinderle. BPA, RCA and ACA have a labeling pattern in the human colon that is complementary to *Dolichos biflorus* agglutinin (DBA) and soybean agglutinin (SBA). These latter lectins label goblet cell mucin in the upper half of the crypt, in those epithelial cells that have migrated into the zone of differentiation. See Boland. DBA and SBA appeared histochemically to bind preferentially to goblet cell mucin. BPA and RCA label mucins in the lower crypt region, but as previously mentioned, also labeled cytoplasmic structures throughout the crypt. In this study, we found that ACA labels cytoplasmic and membrane-bound structures, and tends not to label goblet cell mucin in the normal colon. Secreted glycoconjugates are prominently labeled in neoplastic lesions. Therefore, entirely different molecular species may account for the labeling differences between ACA and BPA/RCA.

ACA binding occurs in virtually all neoplastic lesions of the colon, including small adenomas. This is of particular interest since PNA binds to colonic neoplastic lesions at a time point later in their natural history. PNA tends not to label adenomatous polyps less than 1 cm in diameter, and binds to an increasing percentage of neoplastic glands in polyps that are larger, more villous, or more dysplastic, See Boland, C. R., Montgomery, C. K., and Kim, Y. S. *Gastroenterology*, 82: 664–72, 1982. The appearance of glycoconjugates that bind PNA is therefore a relatively late phenomenon in colorectal neoplasia, occurring in the same time frame as genetic mutations in the ras oncogene and deletions on chromosomes, See Volgelstein, B., Pearon, E. R., Hamilton, S. R., Kern, S. E., Preisinger, A. C., Leppert, M., Nakamura, Y., White, R. Smits, A. M. M. Bos. J. L., *N.Engl.J.Med. Med.* 319: 525–532, 1988, and Law, D. J., Olschwang, S., Monpezat, J-P, Lefrancois, D., Jagelman, D., Petrelli, N. J., Thomas, G., Feinbverg, A. P, *Science*, 241: 961–965, 1988. On the other hand, glycoconjugates that bind ACA occur earlier in the natural history of neoplasia, in the time frame reported for gene hypomethylation Goelz, S. E., Vogelstein, B., Hamilton, S. R., Feinberg, A.P., *Science* 228: 187–190, 1985.

ACA-binding glycoconjugates are present in the proliferative region of the normal colon. It is not known whether the structure(s) recognized at the bottom of the colonic crypt are identical to those found in neoplastic tissue, which is a critical issue in need of clarification. ACA prominently labels secreted glycoconjugates in cancers (whereas cytoplasmic structures are the primary sites of labeling in the normal colon), suggesting that modifications in glycosylation may be associated with changes in glycoprotein trafficking.

The identification of T antigen-like structures is highly dependent upon the methods used for their detection. Fluorescein isothiocyanate (FITC)-conjugated PNA does not bind to glycoconjugates in the normal colon. However, using a lectin and antibody technique, as described by Cooper, H. S. *Lab. Invest.*, 47:383–390, 1982, or a polyclonal antibody to T-antigen for immunohistochemical studies as in Yuan, M., Itzkowitz, S. H., Boland, C. R., Kim, Y. S., Tomita, J. T., Palekar, A., Bennington, J. L., Trump, B. F., and Kim, Y. S. *Cancer Res.*, 46: 4841–4847, 1986. Labelling at the base of the crypt has been reported in a small proportion (approximately 5%) of normal colons reviewed above in reference to Boland, C. R. (G. Steele, R. W. Burt, S. J. Winawer, and J. P. Karr (eds)), *Basic and Clinical Perspectives of Colorectal Polyps and Cancer*, pp. 277–287, New York, N.Y., A. L. Liss, Inc., 1988. This has created confusion regarding the synthesis of T-antigen by normal colonic epithelium, which has been exacerbated by a detailed study of mucin oligosaccharides from the normal colon that failed to detect the T-antigen or any "cryptic" variations, See Podolsky, D. K. "Oligosaccharide structures of human colonic mucin," *J. Biol. Chem.*, 260: 8262–8271, 1985, and, Podolsky, D. K., *J. Biol. Chem.*, 260: 15510–15515, 1985. It is now apparent that T-antigen is not abundantly expressed in the normal colon, although a cryptic variant of T-antigen may be presented with chain extension or substituents on the C'2,C'3,C'4 or C'6 positions of the galactose residue that would interfere with recognition by PNA. A candidate variation of the T-antigen that may be present in the normal colon is the disialylated tetrasaccharide-Neu5Ac $\alpha$2,3Gal$\beta$1, 3(Neu5Ac$\alpha$2,6) GalNAc, which has not yet been identified in the colon. However, the failure of neuraminidase to uncover PNA-binding sites in the normal colon would militate against this. Additional forms such as the monosialylated trisaccharide in which only the $\alpha$2,6-linked sialic acid remains, or the non-sialylated native T-antigen, appear to be expressed in neoplastic epithelium. This speculation was supported by the experiments in which cancer specimens were treated with neuraminidase. Removal of $\alpha$2,3-linked sialic acid enhanced labeling by PNA, but had no effect on labeling by ACA. Additional characterization of the mucin-type oligosaccharides from colonic neoplasia is necessary to confirm this hypothesis.

FAP is a genetic disease in which the normal restraints on epithelial cell proliferation eventually fail, the colon develops a large number of adenomatous polyps, and colonic cancer inevitably ensues. Prior investigators have used thymidine incorporation studies, as in Deschner, E. E., Lewis, C. M., Kipkin, M. *J.Clin. Invest.* 42: 1922–1928, 1963, and measurement of ornithine decarboxylase, as in Luk, G. D., Baylin, S. B., *N.Engl. J.Med.*, 311: 80–83, 1984 to demonstrate expression of the proliferative zone and defective regulation of cell division in the normal-appearing, pre-adenomatous tissue. Both these techniques require the availability of fresh colonic epithelium for their application. Lectin histochemistry may be performed on fixed tissues, including previously obtained archival specimens, because of the stability of carbohydrate structures during the fixation and embedding procedures. The labeling by ACA of small adenomas and flat, normal-appearing colonic tissue in FAP is consistent with the previously described defects in proliferation, which distinguishes ACA from PNA. We have recently reported that PNA does not label the flat mucosa or small adenomas in FAP, See Sams. Collectively, this data suggests that early events in colorectal neoplasia such as those associated with defective control of proliferation, may be associated with a form of T antigen recognized by ACA, but that later events such as those seen in larger polyps and cancers, are associated with forms recognized by both ACA and PNA. In any event, ACA and PNA can bind to slightly different carbohydrate structures, which may differ primarily by their state of sialylation.

Potentially the most important histochemical finding with ACA occurred with the tissues obtained from individuals at risk for Hereditary nonpolyposis colorectal cancer, or HNPCC. A subset of these tissues showed labeling with increased intensity and in inappropriate locations compared to normal colons. When labeled with PNA, there was no labeling in HNPCC tissues. See Sams. However, a subset of patients at risk for HNPCC was found which had a significant reduction in the weighted average for labeling with DBA, a lectin that selectively binds to goblet cell mucin in the upper half, or core of differentiation, in the normal colon.

Using ACA, a subset of "outliers" had labeling scores similar to those seen in FAP. If the identification were perfect, only half of our group of patients "at risk" for HNPCC would be carriers of the putative gene for this autosomal dominantly inherited disease. See Boland, C. R. and Troncale, F. J. *Ann.Int.Med.*, 100: 700:701, 1984. Results suggest that a subset of these individuals may have a defect in the control of proliferation that is in some way similar to that in FAP. The fact that only 5/32 had very high ACA-labeling scores could indicate poor identification of the HNPCC trait, heterogeneity in the underlying defect that results in HNPCC, or the failure to sample the appropriate anatomic location in the colon. Furthermore, an abnormality in proliferation or glycoconjugate expression may occur in a limited time frame in the natural history of familial colonic cancer. This promising lead will require additional study in time to determine the clinical outcome in those individuals with abnormal labeling characteristics.

In summary, a new lectin has been used to localize T-antigen variants in samples of human colon. ACA labels the base of the normal colonic crypt of Ueberkuhn, and is abundantly expressed in colonic adenomas and carcinomas. Data suggests that ACA recognizes sialylated variants of the T-antigen that are not recognized by the closely related T-antigen binding PNA lectin. ACA labels epithelial cells not located in the normal zone of proliferation in a small number of normal tissues. Increased intensity of labeling, and labeling outside of the proliferative region are found in normal-appearing FAP tissues, and in the biopsies of a subset of people at risk for HNPCC. ACA may permit the identification of the proliferative pool of cells in the colon, and provides information regarding the oligosaccharide structures associated with this behavior. However, the most valuable potential use of ACA may be in the identification of zones of inappropriate proliferation, such as those present in FAP.

What is claimed is:

1. Amaranthin (ACA) isolated from *Amaranthus caudatus* wherein Amaranthin binds N-acetylgalactosamine.

2. A homodimer lectin isolated from *Amaranthus caudatus* and binding N-acetylgalactosamine having a subunit mass of about 36,000 daltons and having the following amino acid composition in terms of residues per molecule:

Cys about 5.4
Asx about 44.5
Met about 5.7
Thr about 16.1
Ser about 32.8
Glx about 30.6
Pro about 11.5
Gly about 30.2
Ala about 13.3
Val about 20.1
Ile about 16.9
Leu about 27.6
Tyr about 17.0
Phe about 17.0
His about 7.0
Lys about 21.9
Arg about 10.6
Trp about 9.0.

* * * * *